US010888874B2

(12) United States Patent
David et al.

(10) Patent No.: US 10,888,874 B2
(45) Date of Patent: Jan. 12, 2021

(54) METHODS FOR SEPARATION OF MAGNETIC NANOPARTICLES

(71) Applicant: AUBURN UNIVERSITY, Auburn, AL (US)

(72) Inventors: Allan E. David, Auburn, AL (US); Barry Jay Yeh, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 60 days.

(21) Appl. No.: 16/040,096

(22) Filed: Jul. 19, 2018

(65) Prior Publication Data
US 2019/0022664 A1  Jan. 24, 2019

Related U.S. Application Data

(60) Provisional application No. 62/534,325, filed on Jul. 19, 2017.

(51) Int. Cl.
| B03C 1/035 | (2006.01) |
| G01N 35/10 | (2006.01) |
| G01N 33/543 | (2006.01) |
| B03C 1/021 | (2006.01) |
| B03C 1/033 | (2006.01) |
| B03C 1/01 | (2006.01) |
| B03C 1/28 | (2006.01) |

(52) U.S. Cl.
CPC ............... *B03C 1/035* (2013.01); *B03C 1/01* (2013.01); *B03C 1/021* (2013.01); *B03C 1/0335* (2013.01); *B03C 1/288* (2013.01); *G01N 33/54326* (2013.01); *G01N 35/109* (2013.01); *B03C 2201/18* (2013.01); *B03C 2201/26* (2013.01); *C01P 2004/62* (2013.01); *C01P 2004/64* (2013.01); *C01P 2006/40* (2013.01); *C01P 2006/42* (2013.01)

(58) Field of Classification Search
CPC .. B03C 1/035; B03C 1/14; B03C 1/26; B03C 1/288; B03C 1/30; B03C 1/32; B03C 2201/18; B03C 2201/20; B03C 2201/22; B03C 2201/26; B03C 1/01; B03C 1/021; B03C 1/0335; G01N 35/109; G01N 35/54326; G01N 35/54346; G01N 15/0656; G01N 2015/1081
See application file for complete search history.

(56) References Cited

U.S. PATENT DOCUMENTS

| 7,131,537 | B2 * | 11/2006 | Papadimitrakopoulos | ................... B01D 15/34 209/18 |
| 8,186,515 | B2 * | 5/2012 | Markov | .................. B03C 1/288 209/214 |
| 8,292,083 | B2 * | 10/2012 | Varghese | ............. B03C 1/0332 209/215 |
| 8,697,181 | B2 * | 4/2014 | Biris | .................. A61K 41/0052 427/127 |
| 9,415,399 | B2 * | 8/2016 | Siddiqi | .................... B03C 1/24 |

(Continued)

*Primary Examiner* — Joseph C Rodriguez
(74) *Attorney, Agent, or Firm* — Barnes & Thornburg LLP

(57) ABSTRACT

A method of separating magnetic nanoparticles is described. The method comprises placing the magnetic nanoparticles in a periodic magnetic field. The periodic magnetic field varies between a first magnetic field strength and a second magnetic field strength that is higher than the first magnetic field strength. The nanoparticles may be superparamagnetic iron oxide nanoparticles.

20 Claims, 18 Drawing Sheets

(56) References Cited

U.S. PATENT DOCUMENTS

| | | | |
|---|---|---|---|
| 9,517,938 B2* | 12/2016 | Wainerdi | B03C 1/005 |
| 9,724,705 B2* | 8/2017 | Lee | B03C 1/23 |
| 9,926,195 B2* | 3/2018 | Arnold | B82Y 30/00 |
| 9,999,855 B2* | 6/2018 | Koser | B01L 3/502753 |
| 2009/0309597 A1 | 12/2009 | Horak et al. | |
| 2010/0096581 A1* | 4/2010 | Gleich | B03C 1/01 |
| | | | 252/62.51 R |
| 2010/0108578 A1* | 5/2010 | Dittmer | B03C 1/288 |
| | | | 209/636 |
| 2010/0140146 A1 | 6/2010 | Markov et al. | |
| 2010/0243574 A1* | 9/2010 | Markov | B03C 1/01 |
| | | | 210/695 |
| 2011/0137018 A1 | 6/2011 | Chang-Yen et al. | |
| 2013/0134070 A1* | 5/2013 | Wang | B03C 1/023 |
| | | | 209/3.1 |
| 2013/0265054 A1 | 10/2013 | Lowery, Jr. et al. | |
| 2014/0166545 A1* | 6/2014 | Lyding | B03C 1/023 |
| | | | 209/212 |
| 2014/0305874 A1* | 10/2014 | Stein | B03C 1/01 |
| | | | 210/695 |

* cited by examiner

PRIOR ART

METHODS FOR SEPARATION OF MAGNETIC NANOPARTICLES

CROSS-REFERENCE TO RELATED APPLICATIONS

This application claims priority under 35 U.S.C. § 119(e) to U.S. Provisional Application No. 62/534,325, filed Jul. 19, 2017, which is expressly incorporated by reference herein.

TECHNICAL FIELD

The invention relates to separating magnetic nanoparticles, such as superparamagnetic iron oxide nanoparticles (SPIONs). More particularly, the invention relates to size fractionation of magnetic nanoparticles via a periodic magnetic field.

BACKGROUND

Nanoparticles, such as superparamagnetic iron oxide nanoparticles (SPIONs), attract significant attention in biomedicine and life science applications due to their biocompatibility and magnetic properties. However, the use of nanoparticles for biomedical applications has been hindered by difficulties in controlling nanoparticle size distributions and surface property distributions, which relate to the biodistribution and toxicity of the particles. Particle size distribution may affect the biomedical performance of the particles, such as cellular uptake, pharmacokinetics, and MRI imaging contrast enhancement. In vivo heat efficiency and heat localization are also strongly affected by particle size dispersity. Unfavorable secondary effects of SPIONs such as shock, chest pain, and back pain have been observed in clinical studies. These issues are believed to be due to the broad size distribution of SPIONs that are currently available.

Particle size distribution may be especially difficult to control for particles having sizes between 20 and 150 nm, which may be the preferred size for the majority of biomedical applications such as MRI contrast agents, hyperthermia anticancer treatment, and drug delivery. Conventional separation methods, such as density gradient centrifugation, vacuum filtration, size exclusion gel chromatography, gel chromatography, centrifugation separation, and magnetic field flow fractionation methods (MFFF; also referred to as "MF"), are generally used for purification and have limited ability to control average particle size and particle size distribution.

Therefore, there is a need in the art for improved methods for size selective separation of nanoparticles.

SUMMARY

The present disclosure describes methods for separating magnetic nanoparticles, such as superparamagnetic iron oxide nanoparticles (SPIONs). The methods include a first fractionation step, where the nanoparticles are fractionated by a pulsed magnetic field (PMF). Advantageously, the PMF both attracts particles and allows particles to freely diffuse, enhancing separation. The methods further include a second capture step, where monodisperse populations of fractionated nanoparticles from the first step are captured.

The following numbered embodiments are contemplated and are non-limiting:

1. A method of separating magnetic nanoparticles, the method comprising placing the magnetic nanoparticles in a periodic magnetic field, wherein the periodic magnetic field varies between a first magnetic field strength and a second magnetic field strength that is higher than the first magnetic field strength.

2. The method of clause 1, wherein the first magnetic field strength is less than about 0.2 mT.

3. The method of clause 1 or 2, wherein the first magnetic field strength is about 0 mT.

4. The method of any one of the preceding clauses, wherein the second magnetic field strength is from about 0.1 mT to about 300 mT.

5. The method of any one of the preceding clauses, wherein the second magnetic field strength is from about 0.1 mT to about 50 mT.

6. The method of any one of the preceding clauses, further comprising increasing the second magnetic field strength.

7. The method of clause 6, wherein the second magnetic field strength is increased stepwise.

8. The method of clause 6 or 7, wherein the second magnetic field strength is increased at steps of about 1 mT to about 5 mT.

9. The method of any one of the preceding clauses, wherein the magnetic nanoparticles particles freely diffuse when the periodic magnetic field has the first magnetic field strength.

10. The method of any one of the preceding clauses, wherein the periodic magnetic field varies between the first magnetic field strength and the second magnetic field strength between about 1 and about 20 times before the second magnetic field strength is changed.

11. The method of any one of the preceding clauses, wherein the periodic magnetic field varies between the first magnetic field strength and the second magnetic field strength between about 2 and about 10 times before the second magnetic field strength is changed.

12. The method of any one of the preceding clauses, wherein the periodic magnetic field has the first magnetic field strength for a shorter time than the second magnetic field strength.

13. The method of any one of the preceding clauses, wherein the magnetic nanoparticles form layers that are fractionated based on size, and larger magnetic nanoparticles form fractionated layers closer to a source of the periodic magnetic field than fractionated layers formed by smaller magnetic nanoparticles.

14. The method of any one of the preceding clauses, wherein placing the magnetic nanoparticles in a periodic magnetic field comprises placing the magnetic nanoparticles in a magnetic column.

15. The method of clause 14, wherein the magnetic column is packed with magnetic beads.

16. The method of clause 15, wherein the magnetic beads comprise iron.

17. The method of clause 15 or 16, wherein the magnetic beads have an average size of about 200 μm to about 300 μm.

18. The method of any one of clauses 14 to 17, wherein the particles are blocked from exiting the magnetic column when the periodic magnetic field is applied.

19. The method of any one of the preceding clauses, further comprising applying a flowing fluid to the magnetic nanoparticles after placing the magnetic nanoparticles in the periodic magnetic field.

20. The method of clause 19, wherein the periodic magnetic field is replaced by a continuous magnetic field when the flowing fluid is applied.

21. The method of clause 20, wherein the continuous magnetic field is decreased during the applying step to release fractionated layers of magnetic nanoparticles.

22. The method of clause 21, wherein the continuous magnetic field is decreased stepwise.

23. The method of any one of clauses 19 to 22, wherein the velocity of the flowing fluid is increased during the applying step to release fractionated layers of magnetic nanoparticles.

24. The method of any one of clauses 19 to 23, wherein the solvent of the flowing fluid is changed during the applying step to release fractionated layers of magnetic nanoparticles.

25. The method of any one of clauses 19 to 24, wherein the ionic strength of the flowing fluid is changed during the applying step to release fractionated layers of magnetic nanoparticles.

26. The method of any one of clauses 19 to 25, further comprising capturing fractionated layers of magnetic nanoparticles that are released during the applying step.

27. The method of clause 26, wherein the fractionated layers of magnetic nanoparticles that are released during the applying step are captured by a second magnetized column.

28. The method of any one of the preceding clauses, wherein the magnetic nanoparticles comprise two or more populations of magnetic nanoparticles having different compositions.

29. The method of clause 28, wherein the magnetic nanoparticles form layers that are fractionated based on composition.

30. The method of any one of the preceding clauses, wherein the magnetic nanoparticles are paramagnetic.

31. The method of any one of the preceding clauses, wherein the magnetic nanoparticles are superparamagnetic.

32. The method of any one of the preceding clauses, wherein the magnetic nanoparticles comprise iron.

33. The method of any one of the preceding clauses, wherein the magnetic nanoparticles comprise iron oxide.

34. The method of any one of the preceding clauses, wherein the magnetic nanoparticles are coated.

35. The method of any one of the preceding clauses, wherein the magnetic nanoparticles are coated with starch.

36. The method of any one of the preceding clauses, wherein the magnetic nanoparticles are aminated.

37. The method of any one of the preceding clauses, wherein the magnetic nanoparticles are PEGylated.

38. The method of any one of the preceding clauses, wherein the magnetic nanoparticles comprise two or more populations of magnetic nanoparticles having different coatings.

39. The method of clause 38, wherein the magnetic nanoparticles form layers that are fractionated based on coating.

40. The method of any one of the preceding clauses, wherein the magnetic nanoparticles have a polydispersity index (PdI) of greater than about 0.1 prior to placing the magnetic nanoparticles in the periodic magnetic field.

41. The method of any one of the preceding clauses, wherein the magnetic nanoparticles have a PdI of greater than about 0.3 prior to placing the magnetic nanoparticles in the periodic magnetic field.

42. The method of any one of the preceding clauses, wherein a fraction of the magnetic nanoparticles having a PdI of less than about 0.15 is isolated.

43. The method of any one of the preceding clauses, wherein a fraction of the magnetic nanoparticles having a PdI of less than about 0.1 is isolated.

44. The method of any one of the preceding clauses, wherein a fraction of the magnetic nanoparticles having a PdI of less than about 0.05 is isolated."

45. The method of any one of the preceding clauses, wherein a fraction of the magnetic nanoparticles having an average particle size of about 10 nm to about 200 nm is isolated.

46. The method of any one of the preceding clauses, wherein a fraction of the magnetic nanoparticles having an average particle size of about 10 nm to about 50 nm is isolated.

47. The method of any one of clauses 1 to 45, wherein a fraction of the magnetic nanoparticles having an average particle size of about 50 nm to about 150 nm is isolated.

48. A magnetic nanoparticle having a PdI of less than 0.1.

49. A magnetic nanoparticle having a PdI of less than 0.05.

50. The magnetic nanoparticle of clause 48 or 49, wherein the magnetic nanoparticle is paramagnetic.

51. The magnetic nanoparticle of any one of clauses 48 to 50, wherein the magnetic nanoparticle is superparamagnetic.

52. The magnetic nanoparticle of any one of clauses 48 to 51, wherein the magnetic nanoparticle comprises iron.

53. The magnetic nanoparticle of any one of clauses 48 to 52, wherein the magnetic nanoparticle comprises iron oxide.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 shows a schematic view of the procedure for conventional MFFF where the magnetic column is magnetized, SPIONs are introduced with a gravity fluid flow, the exit fluid is added back to the column until it turns clear because all SPIONs are captured by the magnetic column, the column is connected to a hydraulic pump and a second magnetic column, and the current within the electric coil is reduced stepwise.

FIG. 2 shows a schematic view of the procedure for DMF where the exit of a magnetic column is blocked and the column is fill with a suspension of SPIONs, the magnetic column is magnetized by a PMF such that SPIONs are captured and released repeatedly until layers form, the system is connected to a hydraulic pump and a second magnetic column, and the current is reduced stepwise to release multiple fractionations.

Figure 15:
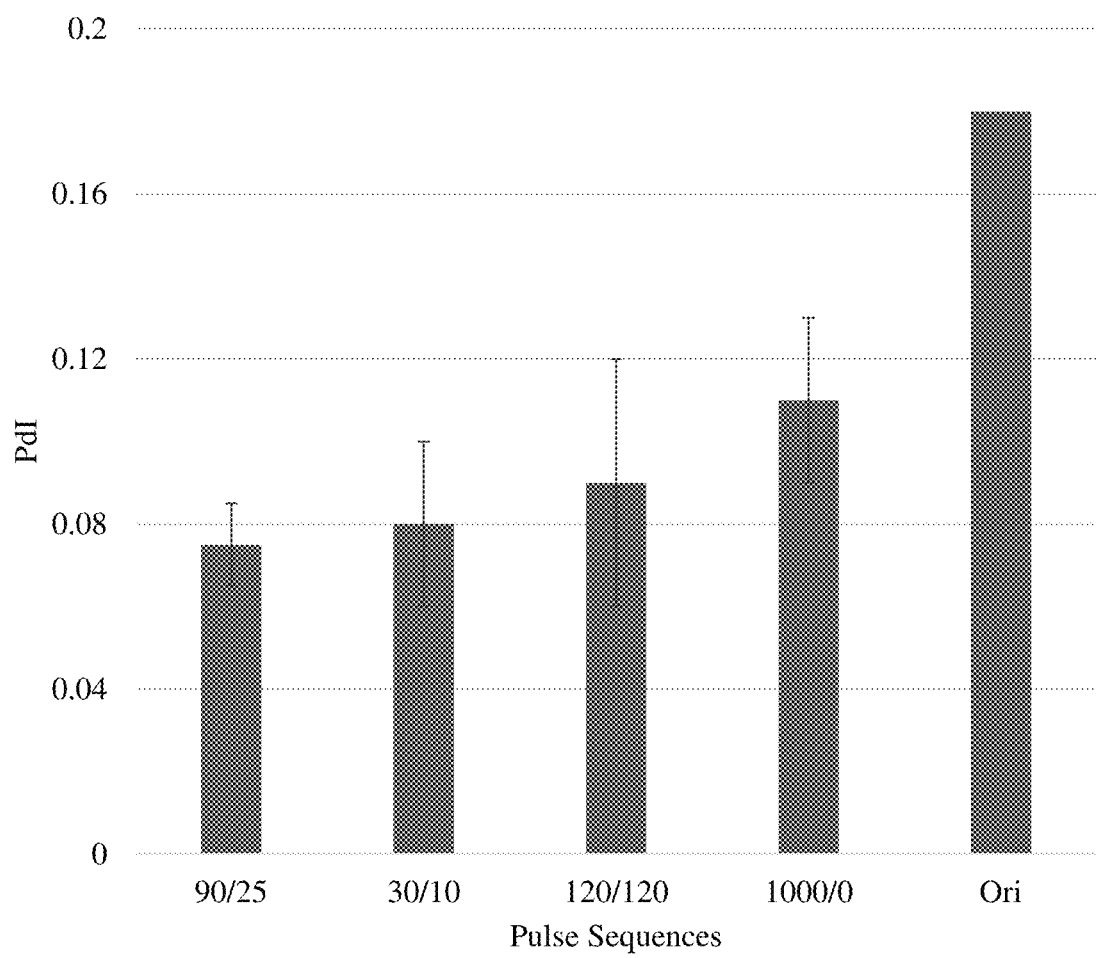

FIG. 15 shows a chart of PdI after various DMF pulse sequences were applied to uncoated SPIONs, including a pulse width of 90 seconds and 25 seconds between pulses, a pulse width of 30 seconds and 10 seconds between pulses, a pulse width of 120 seconds and 120 seconds between pulses, and a pulse width of 1000 seconds and 0 seconds between pulses.

Figure 16A:
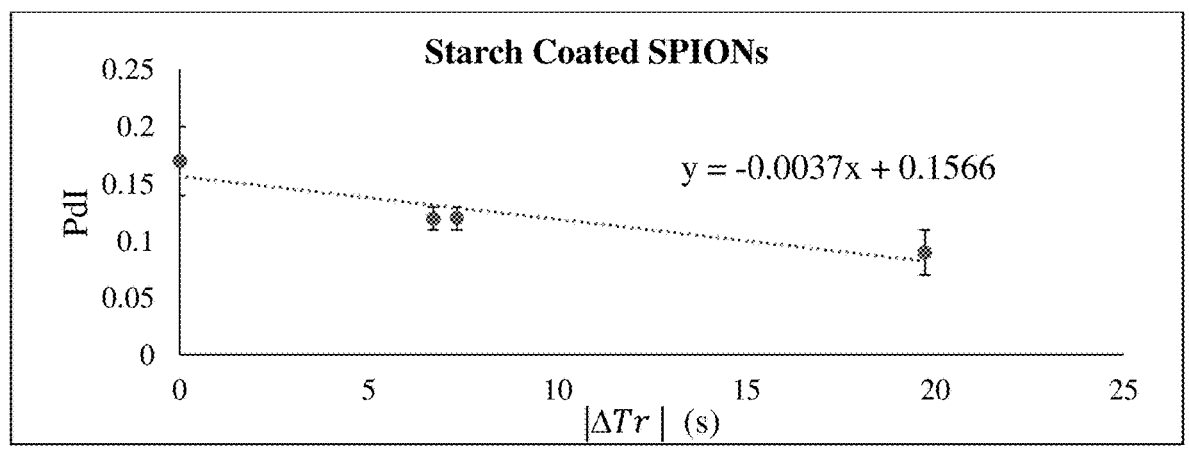

FIG. 16A shows a chart of experimentally determined PdI compared to calculated capture times for starch-coated SPIONs.

Figure 16B:
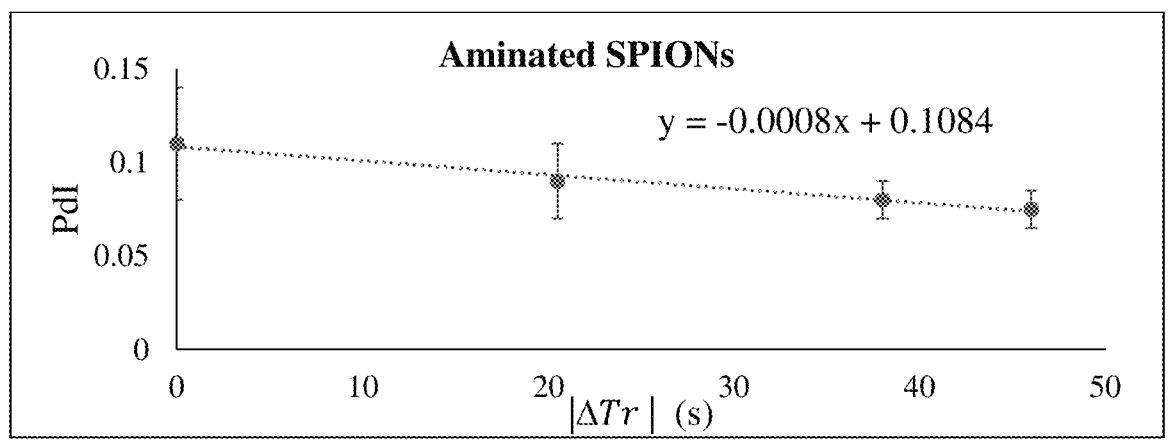

FIG. 16B shows a chart of experimentally determined PdI compared to calculated capture times for aminated SPIONs.

Figure 16C:
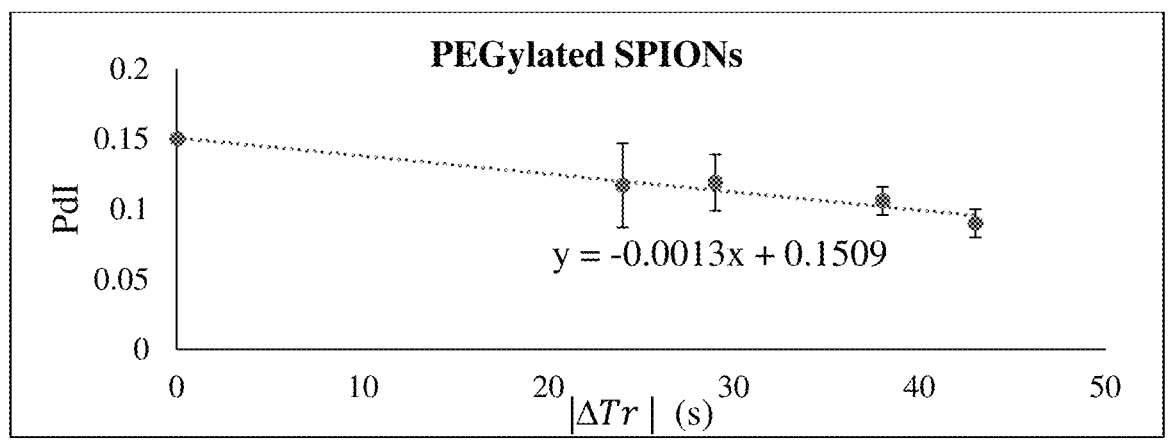

FIG. 16C shows a chart of experimentally determined PdI compared to calculated capture times for PEGylated SPIONs.

DETAILED DESCRIPTION

Various embodiments of the invention are described herein as follows. In one embodiment, diffusive magnetic fractionation (DMF) methods for separating magnetic nanoparticles are provided. DMF is a size fractionation method that includes applying a pulsed magnetic field (PMF) to a population of magnetic nanoparticles. By applying a PMF rather than a continuous magnetic field, DMF separates nanoparticles based on both magnetic mobility (when the field is on) and diffusivity (when the field is off). As such, the methods presented herein allow for greater selectivity of magnetic nanoparticles and improve the size homogeneity of nanoparticles. DMF retains the same advantages as the MFFF, such as scalability and high particle recovery, with significant improvements in performance.

In some embodiments DMF is performed as a two-step process to separate nanoparticles by size or other differences. For example, disclosed herein is a methodology to purify nanoparticles based on composition or surface properties. In a first fractionation step, particles are separated in a stationary phase based on their size differences by a PMF. Once the particles are separated, they are captured in a second step. By initially forming stationary layers through application of a PMF, followed by releasing already-separated particles, the method solves various shortcomings of methods previously known in the art.

As such, DMF may be utilized to separate differently sized nanoparticles, such as superparamagnetic iron oxide nanoparticles (SPIONs). These nanoparticles have a variety of applications that are enhanced by fractionation using DMF. For example, the resulting monodisperse nanoparticles may be used as magnetic resonance imaging (MRI) contrast agents, for magnetic hyperthermia treatment (MHT), for tissue repair, for drug delivery, for detoxification of biological fluid, etc.

In the first step, nanoparticles are separated by applying a PMF to an otherwise stationary nanoparticle suspension. By using a PMF, DMF utilizes the differences in diffusivity and magnetic mobility of differently sized particles (or particles having different compositions). It is to be understood that nanoparticles are captured from a motionless fluid body in DMF.

First, the suspension is placed in a magnetic column that is packed with soft iron beads. The iron beads inside the column enhance the external magnetic field and provide a larger surface area for particles to settle. The exit of the magnetic column is blocked to prevent leakage. The magnetic column is inside an electric coil, which provides the PMF to magnetize the iron beads periodically.

PMF provides pulses that vary between higher strength and lower strength magnetic fields. At the higher strength magnetic fields, the beads are magnetized, and the particle suspension is attracted to the PMF source. Differently sized nanoparticles move toward the magnetic source at various rates during magnetic pulses. In particular, magnetic attraction increases with particle size. As such, when the PMF is actively applying a magnetic field, larger particles experience strong magnetic attraction and move more quickly to the source of the magnetic field than smaller particles. In a preferred embodiment, the larger particles are immobilized to the PMF source before lowering the strength of the magnetic field.

Between pulses, the PMF applies a magnetic field of a lower strength, or stops applying a magnetic field. When the PMF is at the lower strength, the iron beads are demagnetized, and nanoparticles freely diffuse away from the magnetic source due to the absence of the magnetic field. The smaller particles diffuse away from the magnetic source more quickly than larger particles, thus further separating the particles based on size.

Without intending to be bound by theory, it is believed that by periodically repeating this process without flow, potential issues with larger nanoparticles being blocked by smaller nanoparticles from reaching the magnetic source, such as the issues observed with MFFF methods, are resolved. Eventually, larger particles will be trapped in an inner layer due to having slower diffusion rates and stronger magnetic attraction. On the other hand, smaller nanoparticles will be forced to settle on the outer layer owing to weaker attraction and faster diffusion rates.

The higher strength of the PMF may be about 0 to about 1000, about 0 to about 500, about 0 to about 300, about 0 to about 200, about 0 to about 100, about 0 to about 50, about 0 to about 30, about 0 to about 25, about 0 to about 20, about 0.03 to about 1000, about 0.03 to about 500, about 0.03 to about 300, about 0.03 to about 200, about 0.03 to about 100, about 0.03 to about 50, about 0.03 to about 30, about 0.03 to about 25, about 0.03 to about 20, about 2 to about 1000, about 2 to about 500, about 2 to about 300, about 2 to about 200, about 2 to about 100, about 2 to about 50, about 2 to about 30, about 2 to about 25, about 2 to about 20, about 5 to about 50, about 5 to about 30, about 5 to about 25, or about 5 to about 20 mT. In some embodiments, the magnetic field strength may be about 24.8 mT for PEG coated nanoparticles, about 16.5 mT for amine coated nanoparticles, or about 8.25 mT for starch coated nanoparticles. These magnetic strengths may be accomplished by applying a current of about 0 to about 1000, about 0 to about 400, about 0 to about 350, about 0 to about 250, about 0 to about 50, about 5 to about 1000, about 5 to about 400, about 5 to about 350, about 5 to about 250, or about 5 to about 50 mA to a 22 W electrical coil. It is to be understood that the current may be a direct current (DC) or an alternating current (AC). For example, when the current is AC, the magnetic field strength is based on the amplitude of the AC current rather than the net current. The lower strength of the PMF may be about 0 to about 5, about 0 to about 1, about 0 to about 0.5, about 0 to about 0.1 mT.

The PMF may apply several pulses to improve fractionation of particles. In some embodiments, about 1 to about 50, about 1 to about 30, about 1 to about 20, about 1 to about 10, about 2 to about 50, about 2 to about 30, about 2 to about 20, about 2 to about 10, about 5 to about 50, about 5 to about 30, about 5 to about 20, or about 5 to about 10 pulses are applied.

The PMF may be configured such that the higher strength and lower strength portions of the PMF are applied for various amounts of time. In each period, the higher strength of the PMF may by applied for about 5 seconds to about 5 minutes, about 5 seconds to about 2 minutes, about 5 seconds to about 90 seconds, about 5 seconds to about 75 seconds, about 5 seconds to about 60 seconds, about 30 seconds to about 5 minutes, about 30 seconds to about 2 minutes, about 30 seconds to about 90 seconds, about 30 seconds to about 75 seconds, about 30 seconds to about 60 seconds, about 60 seconds to about 5 minutes, about 60 seconds to about 2 minutes, about 60 seconds to about 90 seconds, about 60 seconds to about 75 seconds, about 30 seconds, about 45 seconds, about 70 seconds, about 80 seconds, or about 110 seconds. In each period, the lower strength of the PMF may by applied for about 1 second to about 60 seconds, about 1 second to about 45 seconds, about 1 second to about 30 seconds, about 1 second to about 20 seconds, about 5 second to about 60 seconds, about 5 second to about 45 seconds, about 5 second to about 30 seconds, about 5 second to about 20 seconds, about 10 second to about 60 seconds, about 10 second to about 45 seconds, about 10 second to about 30 seconds, about 10 second to about 20 seconds, about 5 seconds, about 10 seconds, about 15 seconds, about 20 seconds, about 25 seconds, about 30 seconds, or about 35 seconds.

Next, the higher strength portion of the PMF may be increased in a gradual or stepwise manner such that larger nanoparticles are captured before smaller nanoparticles. By increasing the strength of the PMF, the magnetic field eventually becomes strong enough to trap smaller nanoparticles. The higher strength portion of the PMF may be increased at increments of about 0.1 to about 5, about 0.5 to about 5, about 1 to about 5, about 0.1 to about 3, about 0.5 to about 3, or about 1 to about 3 mT.

After multiple cycles, differently sized nanoparticles are separated by their different attraction and diffusion rates into multiple monodisperse fractionations. Each fractionation includes similarly sized particles. A layered structure of differently sized SPIONs is eventually formed on the iron beads and may be maintained when a constant magnetic field replaces the PMF. Therefore, the particles are moved into different layers after multiple pulses, where the larger sized particles are closer to the magnetic source than the smaller ones.

In a second step, the fractionated particles are released. In some embodiments, after particles are captured during the first step, a continuous (not pulsed) magnetic field is applied and the strength of the continuous magnetic field is decreased stepwise to release differently sized nanoparticles layer by layer. The system may include a hydraulic pump to provide a fluid flow during the second step to carry released nanoparticles from the magnetic column to a collector. The collector may be a column magnetized by a strong magnetic. Small SPIONs release first because of the weak magnetic attraction caused by their low magnetic content and position far away from the magnetic source. Alternatively, particles may be released by changing the solvent or ionic strength of the fluid flow.

It is contemplated that the methods of the present disclosure may further comprise an additional size-selection process. For example, nanoparticles may be subjected to a size-selection process before use of DMF.

In some embodiments, the additional size-selection process includes adding poor solvent to precipitate larger particles. When poor solvent is added into a poly-dispersed particle mixture, larger particles will precipitate faster than the smaller ones. In some embodiments, particles can be separated by centrifugation. It is further contemplated that the secondary process may be selected from the group consisting of magnetic fractionation, centrifugation, gel chromatography, and vacuum filtration.

In some embodiments, DMF can be monitored by nanoparticle concentration. For example, a computer may be programmed to determine when to decrease the strength of the magnetic field holding fractionated particles, thereby releasing the particles. As such, DMF may be carried out as a continuous and/or fully automated process.

For example, the process may be automated with the addition of an electrometer and a computer. The electrometer may be used measure the fluid resistivity and monitor separation progress with changes in nanoparticle concentration. In some embodiments, the computer is programmed such that once all nanoparticles are captured, the power supply will decrease the current output automatically and thereby release larger nanoparticles. Once the current reaches zero and all particles pass through the system, new particles may be injected into the system and the separation process repeated.

The methods of the present disclosure may be used to fractionate various types and sizes of nanoparticles. In some embodiments, the nanoparticles are paramagnetic. In some embodiments, the nanoparticles are superparamagnetic. Superparamagnetism may prevent particles from aggregating. In some embodiments, the particles only have a single magnetic domain. In some embodiments, the particles are not ferromagnetic. In some embodiments, particles may have a magnetic saturation of about 30 to about 50 emu/g.

In some embodiments, the nanoparticles comprise metal. For example, the nanoparticles may comprise iron or gold. In some embodiments, the iron may be iron oxide. For example, the iron oxide may be magnetite ($Fe_3O_4$). The iron oxide may be $Fe_3O_4/\gamma\text{-}Fe_2O_3$.

Particles may have various shapes. Particles' shapes may depend on the particles' compositions and/or methods of synthesis. In some embodiments, the particles' shapes may be spherical or cubic.

Additionally, the nanoparticles may be single-core nanoparticles or may be multi-core nanoparticles. In some embodiments, single-core nanoparticles have an average size of less than about 20 nm. In some embodiments, multi-core nanoparticles have an average size of greater than about 20 nm.

It is contemplated that iron oxide nanoparticles may be synthesized with shell and core structure. The core material may be magnetite. In some embodiments, the nanoparticles are multi-core nanoparticles having iron oxide cores of about 5 to about 15 nm.

Multi-core nanoparticles may comprise various materials known to those skilled in the art. The modifications may create a charged coating or a polymer coating. An iron oxide core may be aminated. Also, an iron oxide core may be PEGylated. The iron oxide core may be coated with starch. Starch coated SPIONs may be cross-linked, aminated, and PEGylated according to methods known in the art. In some embodiments, nanoparticle cores may be held together by long chain polymers. Multi-core nanoparticles may comprise a shell material formed by PEGylation, where a poly(ethylene glycol) coating can improve the biocompatibility of the nanoparticle. Dextran and Polyvinylpyrrolidone (PVP) coatings may be formed to enhance blood circulation time. The particles may be carboxydextrane-coated. Polyvinyl alcohol (PVA) coatings may be formed to prevent aggregation and narrow the size distribution of the nanoparticles.

The particles may be synthesized by a variety of methods known in the art. For example, single-core particles may be synthesized by a method selected from the group consisting of gas phase deposition, electron beam lithography, chemical precipitation, hydrothermal decomposition, and microemulsion.

After synthesizing single-core particles, these particles can be further reacted to generate multi-core particles. Most multi-core particles are synthesized by the same process as single-core particles with further modification, such as silanisation, starch addition, and PEGylation to obtain multi-core particles.

In some embodiments, the particles may be formed using a polyol method. With a polyol method, the particles are directly coated with hydrophilic polyol ligands. The polyol may serve as a solvent, reducing agent, and stabilizer. The polyol method may be based on alkaline hydrolysis of $Fe^{2+}$ and/or $Fe^{3+}$ salt in a stoichiometric mixture of polyols, which are diethylene glycol (DEG) and N-methyldiethanolamine (NMDA). The polyol method can also be used with an DEG/NMDA mixture to form citrate coated multi-core flower-shaped particles.

In some embodiments, multi-core particles are formed with an external matrix to stabilize aggregation of precursory single-core particles. Coating materials such as polysaccharides, silica, liposomes, lipids, or polymeric materials may be used form an external matrix.

Ligand exchange methods may be utilized to stabilize particles into a biocompatible aqueous phase. For example, to exchange the surface-coating oleic acid molecules by dimercaptosuccinic (DMSA) molecules, the process involves placing the oleic acid coating particle in toluene mixed with DMSA in dimethylsulfoxide (DMSO) for several hours until the ligands exchange. After the ligand exchange, the particle is washed several times to remove toxic materials.

The methods described herein result in nanoparticle distributions having narrower size distributions compared to convention methods. For example, DMF separated SPIONs (DMF-SPIONs) have an average size distribution at least about 3 times narrower than SPIONs separated by conventional methods. In some embodiments, the size distribution is at least about 4 times narrower or at least about 5 times narrower.

In some embodiments, nanoparticle size distributions are determined by imaging measurements or dynamic light scattering (DLS) measurements. DLS provides a polydispersity index (PdI) to represent the randomness of its measurements. In some embodiments, DLS measurements are performed by utilizing cumulants analysis to estimate the translational diffusivity and calculate the corresponding hydro diameter with Stokes-Einstein relationship. One example of such a calculation is set forth in ISO 13321 and ISO 22412 by Malvern Zetasizer Z S. Alternatively, nanoparticle size distributions may be determined by imaging measurements, such as transmission electron microscopy (TEM), scanning electron microscopy (SEM), or other microscopy approaches, which involve imaging analysis tools to select objects of a specific geometry or size range. Unless stated otherwise, nanoparticle size distributions described herein are based on PdI value.

In some embodiments, prior to fractionation by DMF, the particle mixture has a size distribution of about 10%≤σ≤ about 25%, about 15%≤σ≤ about 25%, about 18%≤σ≤ about 25%, about 10%≤σ≤ about 20%, about 15%≤σ≤ about 20%, or about 18%≤σ≤ about 20%. In some embodiments, after fractionation by DMF, the particle mixture has a size distribution of σ≤ about 10% or σ≤ about 5%.

In some embodiments, prior to fractionation by DMF, the particle mixture has a PdI greater than about 0.1, greater than about 0.2, greater than about 0.3, about 0.1 to about 0.5, about 0.1 to about 0.4, or about 0.1 to about 0.3. In some embodiments, after fractionation by DMF, the particle mixture has a PdI less than about 0.15, less than about 0.1, about 0.01 to about 0.1, about 0.05 to about 0.1, about 0.07, about 0.08, or about 0.09. Accordingly, after fractionation by DMF, PdI may decrease by at least about 25%, at least about 30%, at least about 35%, about 5% to about 95%, about 25% to about 95%, about 35% to about 95%, about 5% to about 90%, about 25% to about 90%, about 35% to about 90%, about 5% to about 80%, about 25% to about 80%, or about 35% to about 80%.

In some embodiments, after fractionation, the particles may have a zeta potential increased by about 0.5 to about 5 mV compared to before fractionation. In some embodiments, greater than about 75%, about 90%, about 95%, or about 97% of the particles are recovered from the DMF process. In some embodiments, DMF scales linearly with the volume of the system.

The nanoparticles of the present disclosure may be used for various applications known in the art, especially those requiring monodisperse nanoparticles. In some embodiments, the nanoparticles of the present disclosure may be used for magnetic resonance imaging (MRI), magnetic hyperthermia treatment (MHT), or drug delivery.

In another embodiment, the methods described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Materials.

FluidMAG-D (starch-coated magnetite (Fe3O4)) iron oxide nanoparticles (75 mg/mL) were obtained from Chemicell® GmBH (Berlin, Germany). Succinimidyl polyethylene glycol (mPEG-NHS) of molecular weight 5 kDa was obtained from Nanocs (New York, N.Y.). Dimethyl sulfoxide (($CH_3$)$_2$50, 99.9%) was obtained from BDH Chemicals. Epichlorohydrin ($C_3H_5ClO$, 99%) was obtained from Alfa Aesar. Sodium hydroxide (NaOH, 97%) was obtained from BDH chemicals. Ferrozine iron reagent, monohydrate was obtained from J. T. Baker. Neocuproine hydrochloride monohydrate ($C_{14}H_{12}N_2 \cdot HCl \cdot H2O$, 99%) was obtained from Acros. Ammonium acetate and ACS ($CH_3COONH_4$, 97% min) were obtained from Alfa Aesar. L-ascorbic acid ($C_6H_8O_6$) was obtained from BDH. Iron standard solution (1.00 mg/L as Fe) was obtained from HACH. Deionized water was obtained by using an ELGA PURELAB Flex water purification system.

SPION Surface Modification Process.

Starch coated SPIONs (FluidMAG-D; Chemicell, Germany) were cross-linked, aminated, and PEGylated. The method started when 2 mL of starch coated SPIONs in aqueous suspension (25 mg/ml) were mixed with 2.6 mL of 6M NaOH (97%) for 15 minutes followed by adding 1.3 mL of epichlorohydrin. The mixture was placed on a shaker for 24 hours. Then the solution was dialyzed with an 8-10 kDa MWCO Float-A-Lyzer® G2 dialysis device (Spectrum Laboratories, Inc., Rancho Dominguez, Calif.) for 24 hours. The dialyzed SPION suspension was then mixed with 2 ml of 30% ammonia at room temperature for 24 hours to provide aminated SPIONs.

These aminated SPIONs were then modified to produce PEGylated SPIONs. The PEGylation process was based on the use of mPEG-NHS (Nanocs; NY). A mixture of 300 µL DMSO, 300 µL water, and 300 µL phosphate buffer was made to dissolve 15 mg of 5 MW of mPEG-NHS (Nanocs, Mass.). Then, 300 µL of aminated SPION suspension was added into the mixture. The final solution was placed on a shaker for 24 hours at room temperature. The resulting PEGylated SPIONs were eventually magnetically separated from the solution and washed with DI-water for 4 times.

Magnetic Column.

An iron bead packed column (LS Column Miltenyi Biotec) was used to increase system capacities. The bottom of the column was sealed with parafilm. The column went through a 22 W electric coil that was connected to a DC power supply (Hewlett Packard 6543A) to provide an external magnetic field. The magnetic field had a linear proportionality with the input current of the electrical coil. Therefore, the input current of the electrical coil may be used to describe the magnitude of the magnetic field.

MF Process (Comparative).

Figure 1:
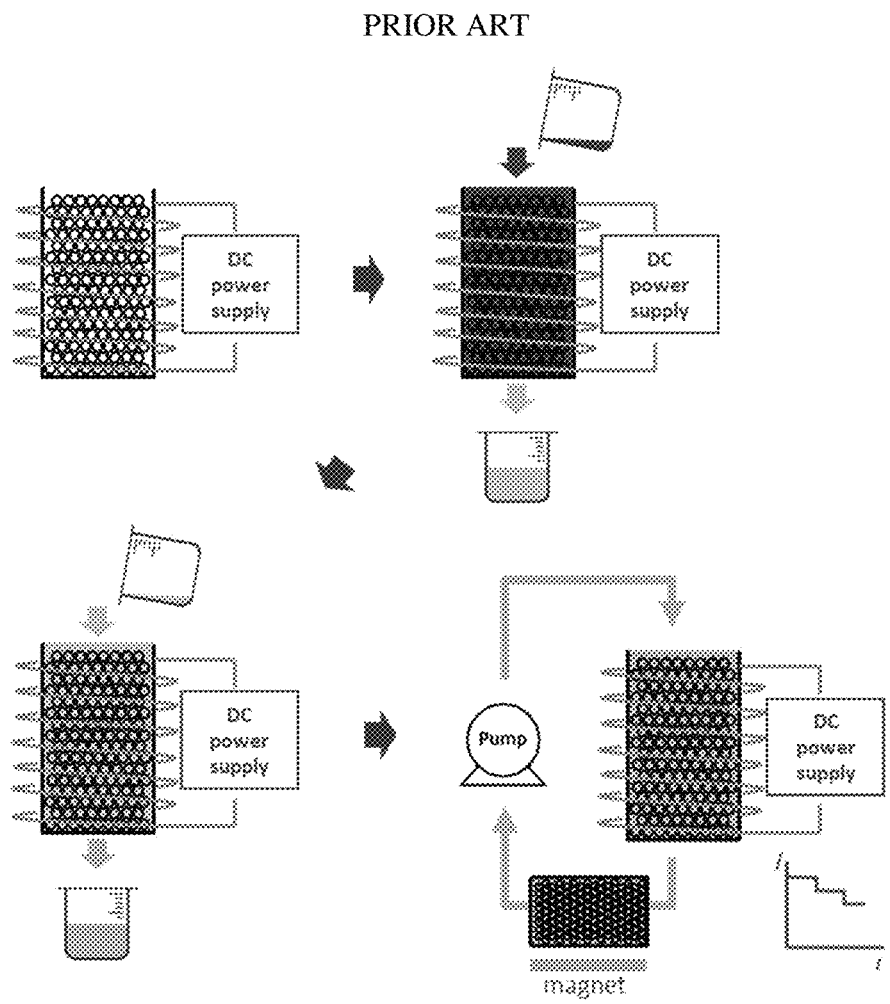

As shown in FIG. 1, a SPION aqueous suspension flowed through the magnetic column by gravity. The column was set at a constant magnetic field of 22 mT. Fluid was collected at the column exit and added back to the top of the column repeatedly until the fluid turned clear. Then a continuous aqueous flow of 1.5 mL/min was introduced into the system by a peristaltic pump, and the field strength was decreased in stepwise manner to release a fractionation at each field strength decrement. During each decrement, the particles were collected from the flow output by a second magnetic column magnetized by a 0.22 T magnet. Each fractionation took between about 5 and about 8 minutes to collect.

The MFFF showed very limited improvement on controlling particle size distribution, which is related the way SPION piles were formed on the beads' surface. Without intending the be bound by theory, it is believed that the constant magnetic attraction of the MFFF prevented some large SPIONs from entering inner layers of the pile due to their original far distance from the surface. These large SPIONs were eventually released with small SPIONs due to their weak magnetic attraction caused by their distance to the beads' surface.

Dmf Process.

Figure 2:
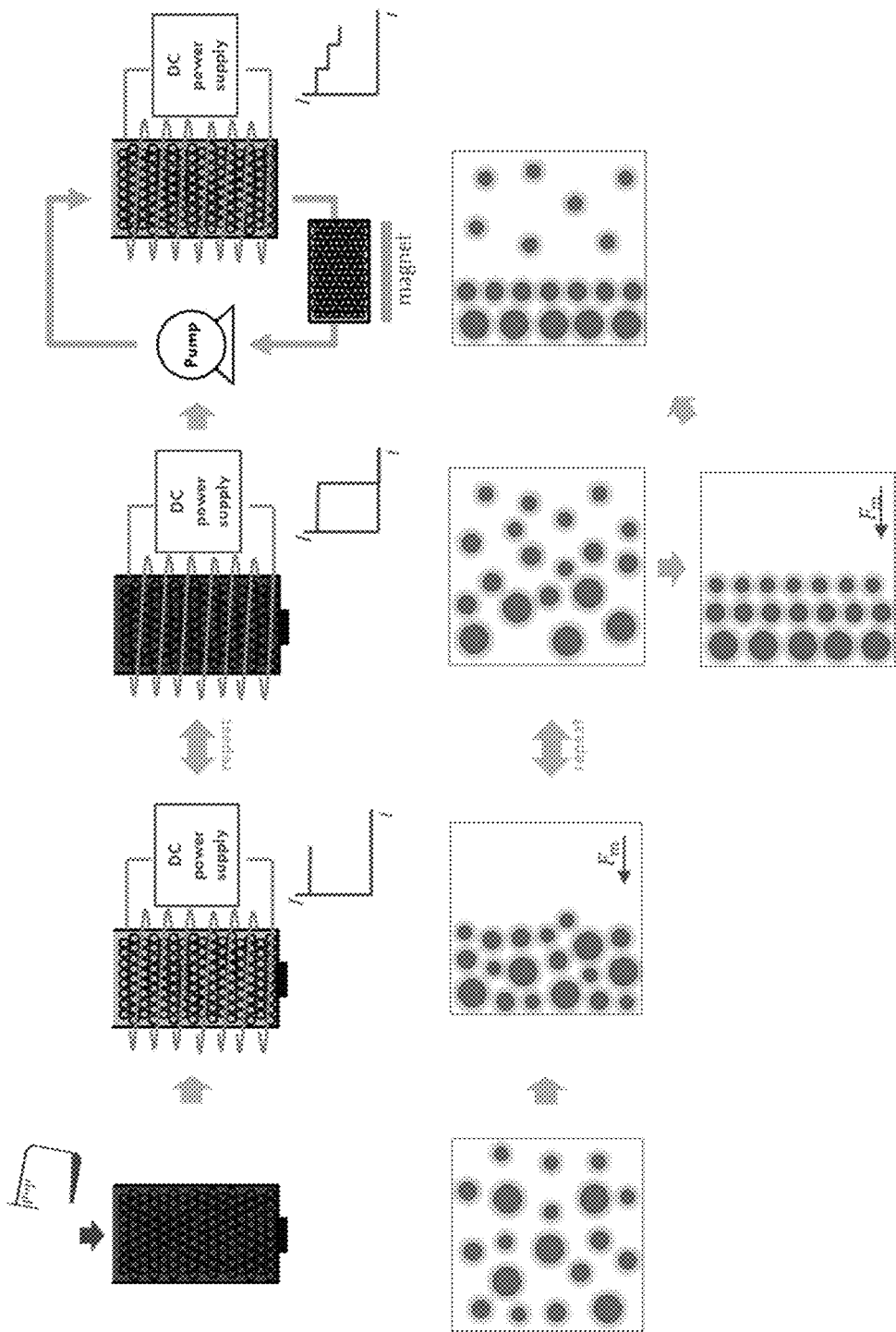

Referring to FIG. 2, a polydisperse SPION solution fully filled the magnetic column. Next, an input current was turned on and off periodically to provide a PMF in multiple cycles. Different PMF cycles and period parameters were used for differently sized and surface coated SPIONs, as is further described herein. In general, the time duration for the on and off cycle was 30 seconds on and 10 seconds off, unless stated otherwise. The current was increased after each cycle, and the settings were 5, 10, 30, 50, 100, 200, 450 mA unless stated otherwise. The magnetic field was maintained constant at 450 mA for 10 minutes once the pulse magnetic field sequence was completed.

After the PMF process was finished, the parafilm on the column was removed and a second column attached. An aqueous flow was then introduced by a peristaltic pump (FH100; Thermo Scientific) at a flow rate of 1.5 mL/min, and then the magnetic field was decreased stepwise to release a fractionation at each decrement. The fractionations were collected until the aqueous solution turned clear, which took about 5 to about 8 minutes. During each decrement, the particles were collected either directly from the flow output or indirectly by a second magnetic column with a strong magnetic field of 0.22 T. Afterward, the magnetic field was reduced again to give multiple fractionations.

Characterization of SPIONs.

A ZetaSizer Nano ZS90 (Malvern, Worcestshire, UK) was used to measure particle hydrodynamic diameters, particle size distributions, and Zeta potentials. Both DLS and Zeta potential measurements were taken in triplicate by the sizing instrument. A Superconducting Quantum Interference Device (Quantum Design, US) was used to measure the magnetic susceptibility of SPIONs. A SpectraMax i3 (Molecular Device, US) was used to measure the optical absorbance of samples.

A ferrozine assay was used to measure the iron content of SPIONs. Iron standards were made by mixing 33.24 uL of stock iron solution at 1000 mg/L with 1123.5 µL, 10 mM HCl and diluted to 0.25, 0.2, 0.15, 0.1, 0.05, 0.02, 0.0075, and 0 nmol/µL. The standards were prepared in triplets and then put into a 24 well plate. SPION samples were made with 1:4000, 1:2000, and 1:1000 dilutions for starch coated SPIONs, aminated SPIONs, and PEGylated SPIONs, respectively. SPION samples were also prepared in triplets and placed in another 24 well plate. Then, 200 µL of iron releasing reagent was added into all of the wells, which were sealed with aluminum foil for both the standards and the SPION samples. The iron releasing reagent was prepared by mixing equal volumes of 4.5% w/v $KMnO_4$ with 1.4 M HCl. Both 24 well plates were vortexed for 1 minute at 650 RPM. Both well plates were incubated for 2 hours at 60° C. and then cooled down for 10 minutes at room temperature. Then, ferrozine was added into all the wells. The ferrozine was prepared by mixing 9.95 mg of ferrozine, 5.12 mg of neocuproine, 578 mg of ammonium acetate, 528 ascorbic acid, and 3 mL of water. Both 24 well plates were incubated at room temperature for 30 minutes. Finally, 280 µL of each sample were transferred from 24 well plate to a 96 well plate and the absorbance was measured at 550 nm.

SPION concentrations were determined by measuring absorbance at 450 nm with 200 µL of volume. Standard curves were obtained by known SPION concentration measured by ferrozine assay.

Separation of SPIONs by MFFF and DMF.

9 fractionations of both MFFF-SPIONs and DMF-SPIONs were produced by fractionating starch coated SPION solutions with input current settings of 300, 200, 100, 50, 30, 20, 10, 5, and 0 mA (resulting in magnetic fields strengths of 24, 16, 8, 4, 2.4, 1.6, 0.8, 0.4, and 0 mT, respectively). Three runs of each of the DMF and MFFF processes, each run producing 9 fractionations, were performed, resulting in a total of 54 fractionations. Both MFFF-SPIONs and DMF-SPIONs were sonicated for 2 minutes and their sizes and size distributions were measured by DLS measurements.

Figure 3:
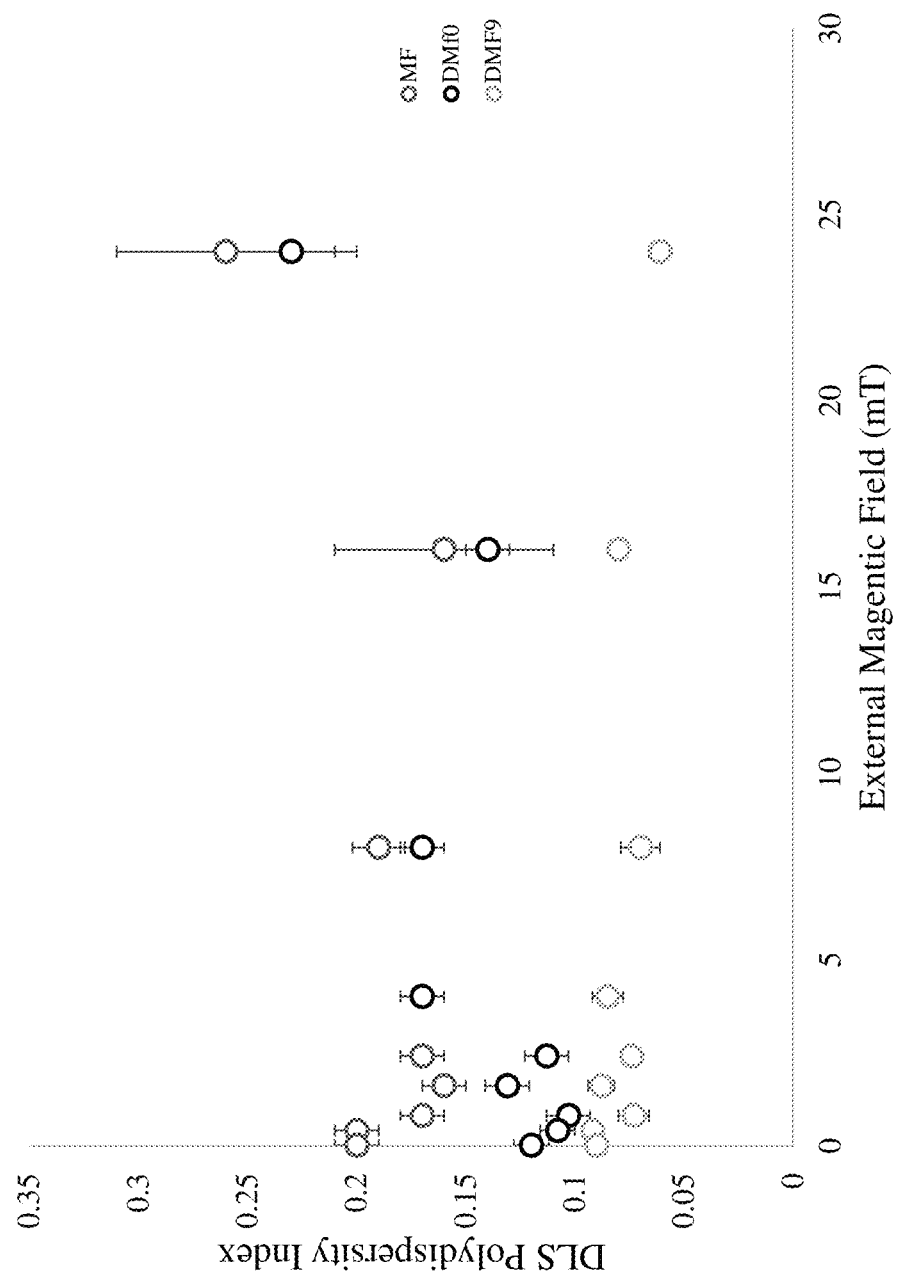
FIG. 3 shows a chart of PdI against magnetic field strength for both MFFF-separated SPIONs and DMF-separated SPIONs, where DMF0 and DMF9 refer to DMF with 0 and 9 PMF cycles, respectively.

DMF was performed with varying numbers of PMF cycles. DMF0 and DMF9 refer to DMF with 0 and 9 PMF cycles, respectively. For example, DMF0 was DMF with 0 PMF cycles. DMF0 was the same as MFFF, except gravity flow was not used to capture the particles. Commercially available polydisperse 105±1.7 nm starch-coated SPIONs with PI values of 0.24 were separated into 9 fractions by the MFFF, DMF0, and DMF9 to compare their general performance on this polydisperse sample. Each of the 9 fractions of MFFF-SPIONs (MFFF-separated SPIONs), DMF0-SPIONs, and DMF9-SPIONs was fractionated at the same magnetic field strengths, which were 24, 16, 8, 4, 2.4, 1.6, 0.8, 0.4, and 0 mT. MFFF-SPIONs, DMF0-SPIONs, and DMF9-SPIONs were measured for their Z-average size and PI by DLS measurements. All samples exhibited significant changes in average particle size among fractionations. All three methods produced SPIONs in range 70-120 nm, as shown in FIG. 3. MFFF-SPIONs had an average PI of 0.18±0.013. DMF0-SPIONs had an average PI of 0.14±0.012. DMF9-SPIONs had an average PI of 0.1±0.01.

Among the 54 fractionations, both the largest and smallest average size fractions were obtained by DMF-SPIONs, indicating a broader separation range. Also, the DMF method significantly improved the PdI by an average of 55% compared to the MFFF method. The size distribution of all nine DMF9-SPION fractions fell within the monodisperse range of PdI≤0.1, as shown in FIG. 3. The Malvern Instrument stated that a PdI value lower than 0.05 was usually only achievable with highly controlled spherical particles. For example, polystyrene spherical nanoparticles were commonly used to calibrate the DLS performances and have a PdI value of 0.05. A PdI of 0.08 was a surprising result at least because SPIONs are usually random shaped particles with collections of multiple iron oxide cores with an external matrix. The result was significantly better than conventional magnetic fractionation (MFFF) method, which resulted in a PdI of 0.17. The DMF method also showed a high particle recovery, scalability, and reproducibility.

DMF9 resulted the narrowest size distribution among three MFFF techniques. DMF9 also had the smallest average sized fraction, which indicated that larger particles were retained by the magnetic column and therefore predominantly the smaller particles were released from the system. The largest fractionations were obtained by both the MFFF and DMF0, but the PdI of the largest MFFF-SPIONs was significantly larger than DMF.

Figure 4:
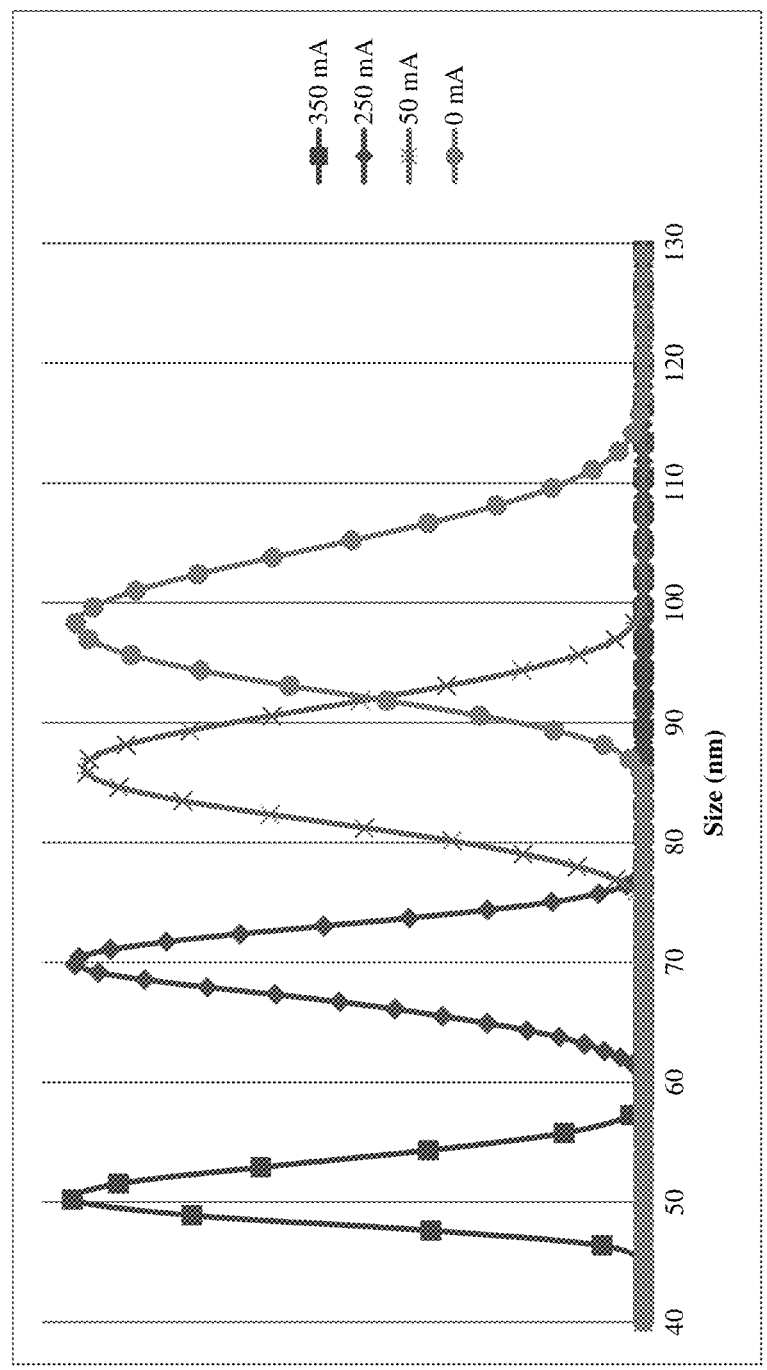
FIG. 4 shows a chart of size distribution of particles resulting from DMF of starch-coated multi-core SPIONs.

FIG. 4 shows a DLS result from separating starch coated multi-core SPIONs using DMF9. The y-axis is intensity-weighted DLS, which is normalized for purposes of comparison. The original particles had an average size of 76.7 nm and distribution of σ=21.8%. Particles were separated into four different sizes of 50.95 nm, 69.53 nm, 86.48 nm, and 98.91 nm, and the resulting size distributions were σ=4.3%, 4.1%, 4.8%, and 5.1%, respectively.

Figure 5:
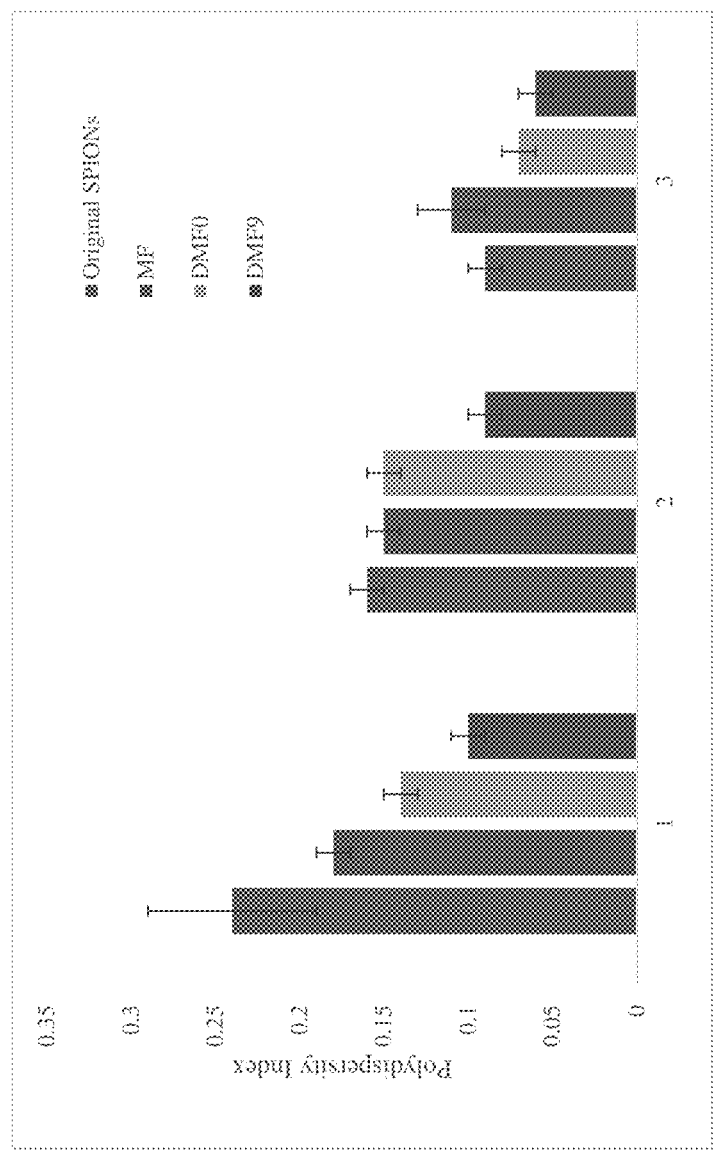
FIG. 5 shows a chart of PdI resulting from MFFF, DMF0, and DMF9 of particles with various starting PdI values, where Groups 1, 2, and 3 are starch-coated SPIONs with PdIs of 0.24, 0.16, and 0.09, respectively.

Additionally, samples with various starting PdI values were investigated using MFFF, DMF0, and DMF9 for effect on resulting PdI. Starch-coated SPIONs with PdIs of 0.24, 0.16, and 0.09 were obtained commercially. All three types of SPIONs were separated by MFFF, DMF0 and DMF9 to observe the performance of each method. As shown in FIG. 5, MFFF resulted in very little to no improvement on particle size distribution when the original sample had a PI value of 0.16 or lower. On the other hand, DMF9 showed significant improvement on all three samples, while DMF0 showed a performance between the MFFF and DMF.

Particle Recovery.

Particle recovery of the DMF was measured. Starch coated SPIONs of 100 nm were used in this experiment. The DMF-SPIONs were measured for sizes and size distributions by DLS. Particles' iron content was measured by ferrozine assay. Iron content was estimated before and after the DMF process.

Polydisperse SPIONs with 0.4 mg of iron were separated into nine fractions of DMF-SPIONs with a total 0.38 mg recovered. Thus, the results indicated a 95% particle recovery by mass. The average size, as determined by volume-weighted DLS measurement, was 90.8 nm, which was very close to the volume weighted average size of the original SPIONs before the DMF separation of 89.7 nm. The average PdI was 0.09.

Separation Based on Surface Chemistry.

Starch coated, aminated, and PEGylated SPIONs were each size separated into 9 fractions by DMF. Three trials were performed on each type of SPION, and DLS was used to measure the size properties and PdI values. An average value based on 27 DMF-SPIONs for each surface coated SPION is reported.

Starch coated SPIONs initially had an average size of 100 nm, a PdI of 0.23, and an average zeta potential of −9 mV. Aminated SPIONs initially had an average size of 110 nm, a PdI of 0.3, and an average zeta potential of +40 mV, which indicates a strong positive charge on the surface. PEGylated SPIONs initially had an average particle size of 145 nm, a PdI of 0.15, and an average zeta potential of +20 mV.

Polydisperse SPIONs with starch, amine, and 5 k MW PEG (polyethylene glycol) coatings were each separated by a DMF9 process. The process for each polydisperse starting sample resulted in a PI of less than 0.1. SPIONs with different surface chemistry were separated using different external magnetic field strengths. To fully immobilize 1 mg Fe of starch, amine, and 5 k MW PEGylated SPIONs, 12, 24, and 34 mT magnetic fields were utilized, respectively.

Figure 6:
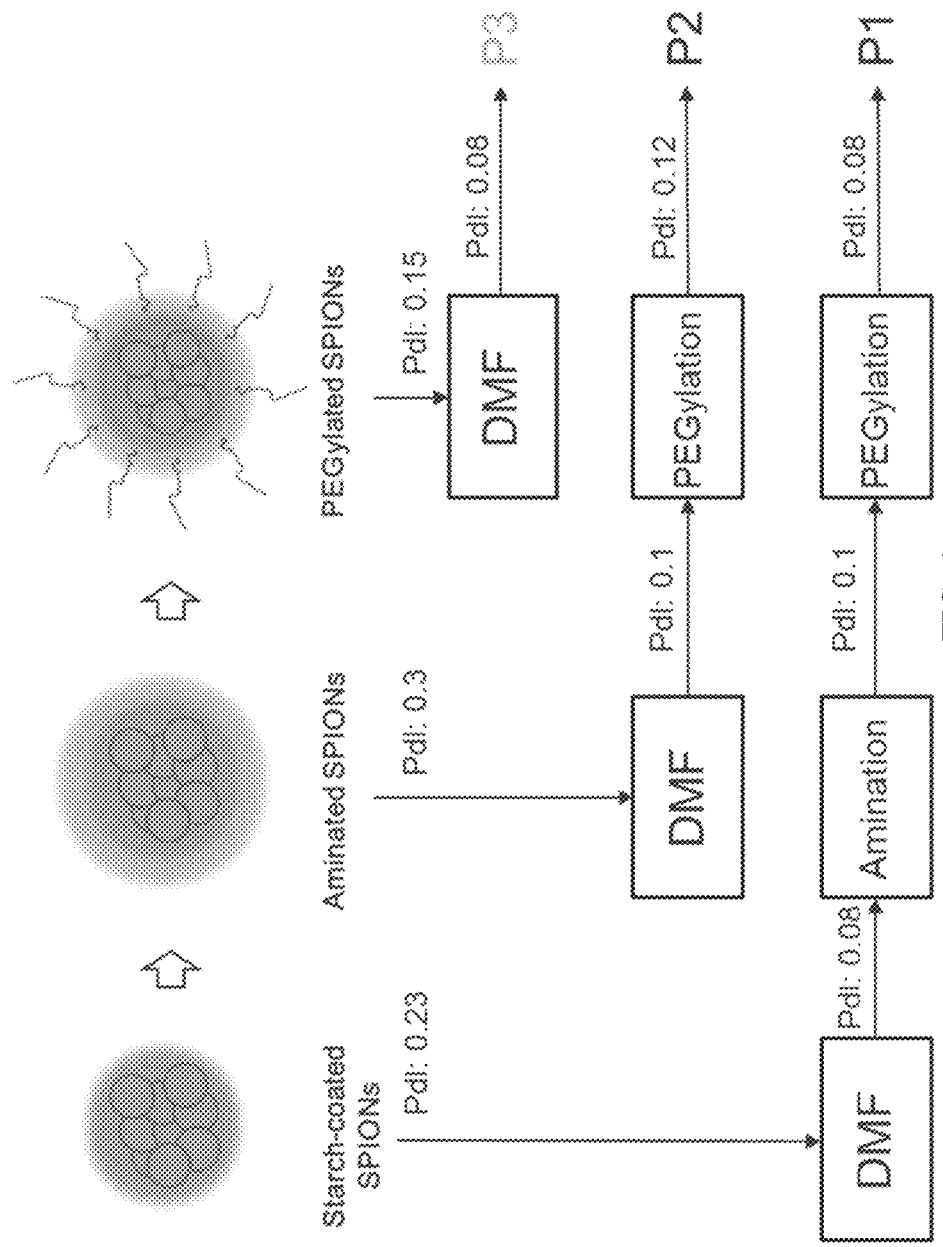
FIG. 6 shows a diagrammatic view for formation and DMF of starch-coated, aminated, and PEGylated SPIONs.

As shown in FIG. 6, three DMF processes were performed on starch coated SPIONs, aminated SPIONs, and PEGylated SPIONs, which represented a starting material, an intermediate product, and a final product, respectively. The first DMF was performed on the starting material, starch coated SPIONs. The resulting separated starch coated SPIONs were further aminated and PEGylated without any further DMF treatment (labeled as P1). The second DMF started with aminated SPIONs. The resulting separated aminated SPIONs were further PEGYlated without any additional DMF (labeled as P2). The third DMF was performed on PEGylated SPIONs (labeled as P3). P1 and P3 showed similar size distributions, each having PdI values of 0.08, while P2 showed a PdI value of 0.12. No significant difference was observed in all three PEGylated SPIONs. Therefore, the DMF can be performed at any stage of the surface modification process based on research preference. The result showed that DMF had the ability to overcome inter-particle interactions.

Figure 7:
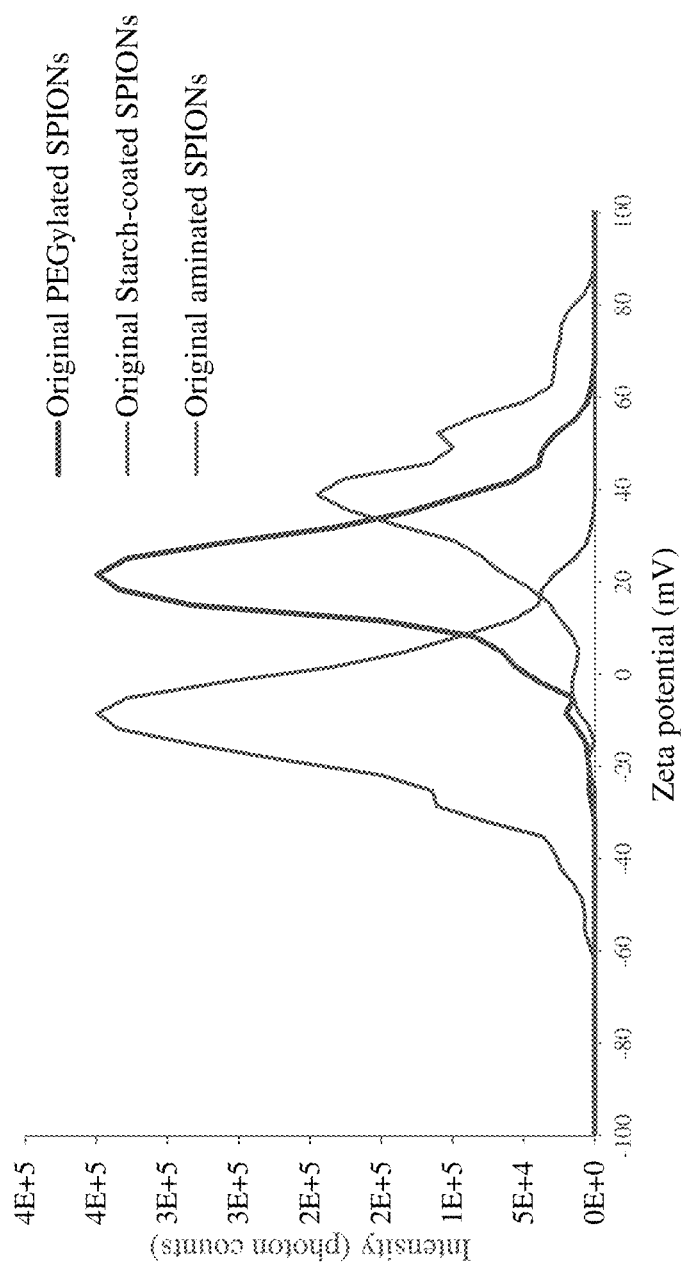
FIG. 7 shows a chart of overlaid zeta potential measurements of starch-coated, aminated, and PEGylated SPIONs before mixture and before DMF.
Figure 8:
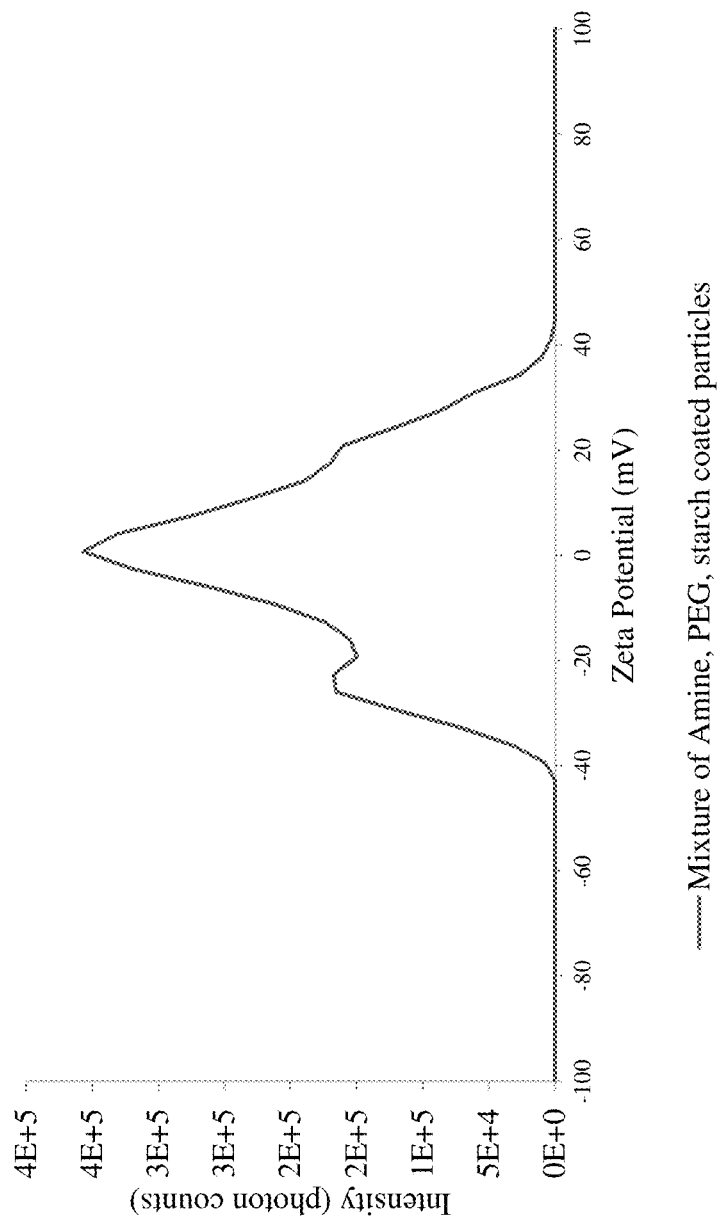
FIG. 8 shows a chart of zeta potential measurements of a 1:1:1 mixture of starch-coated, aminated, and PEGylated SPIONs after mixture and before DMF.
Figure 9:
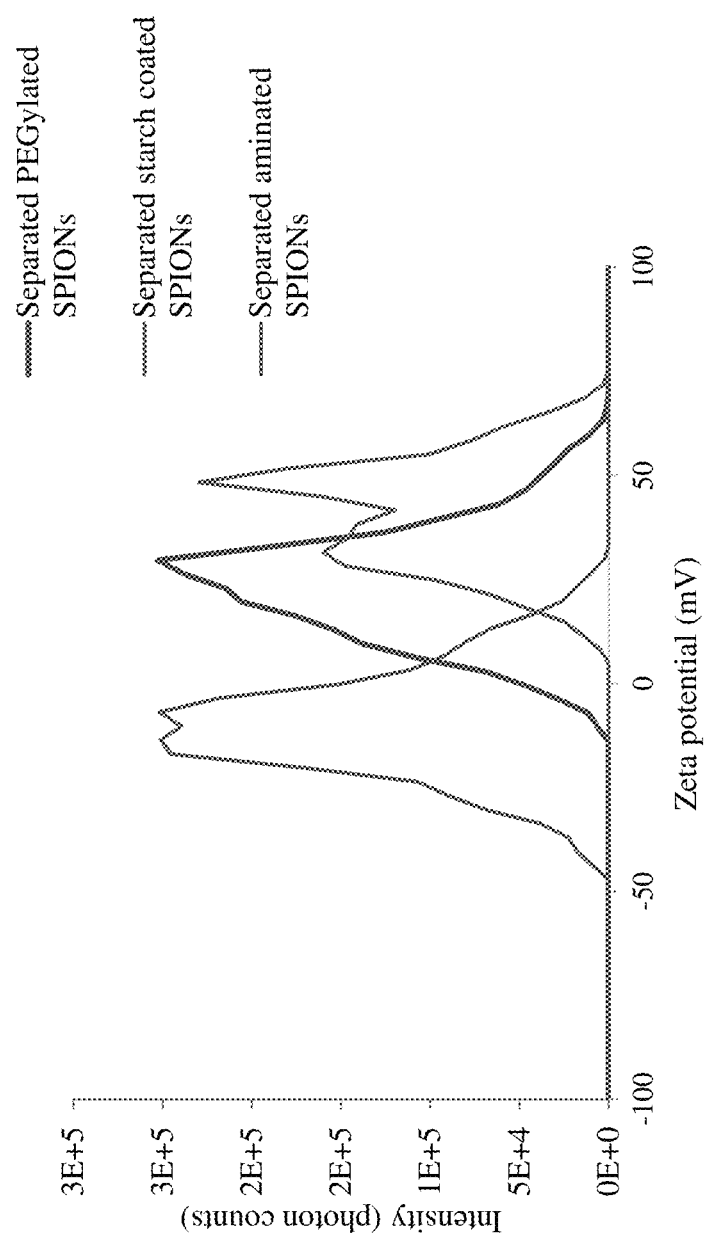
FIG. 9 shows a chart of zeta potential measurements of separated starch-coated, aminated, and PEGylated SPIONs after mixture and after DMF.

The particles were used in a process that separated particles based on different surface chemistry, generating homogenous products. SPIONs with different surface coatings were separated by their size before the surface selection process; so each SPION sample used in this experiment had the same average size of 100 nm. Starch coated, aminated, and PEGylated particles were used in this experiment as three different surface coatings. Then, these particles were mixed together to represent a broad surface chemistry distribution. The mixture was then separated with DMF at three different magnetic field strengths. Zeta-potential was measured before and after the separation to detect differences in surface chemistry, as shown in Table 1. The zeta potentials of the original SPIONs before mixture, the mixture of the original SPIONs, and the separated samples are shown in FIG. 7, FIG. 8, and FIG. 9, respectively.

TABLE 1

Zeta potential measurements of SPIONs before and after the surface separation process.

| Surface | Zeta potential (mV) | Zeta potential after separation (mV) |
| --- | --- | --- |
| PEG | +20.05 | +23.95 |
| Amine | +39.1 | +40.83 |
| Starch | −10.14 | −9.35 |
| Mixture of three (1:1:1) | | −0.93 |

The results showed that different surface coatings could be separated by balancing the hydrodynamic drag force and magnetic force.

Scalability.

Scalability is an advantage of the DMF method for producing large quantities of monodisperse SPIONs at low cost. The performance of the DMF was evaluated by its average PdI values of four DMF9 separations. Four different magnetic columns were designed by varying column volumes to 0.25, 0.5, 0.75, and 1 mL. Three DMF runs and 21 PMF cycles were used to create 4 fractionations from starch coated SPIONs with input currents of 300 mA, 200 mA, 100 mA, and 0 mA. As such, SPIONs were fractionated with magnetic field strengths of 24, 16, 8, and 0 mT. The average PdIs were 0.08, 0.07, 0.07, and 0.07, respectively. This study supports that the DMF can be scaled up without compromising its performance. The results indicated that the system had a linear scalability with volume and the performances were almost not affected.

Mathematical Model.

Computational models were developed to predict the optimal conditions for different particles. The models demonstrated strong agreement with experimental results.

Three parameters affect the performance of the DMF. The first parameter is the interval by which the magnetic field decreases after the layers are formed. A smaller interval will result fractions with narrower distributions. The second parameter is the number of repeating cycles of the PMF at each magnetic field strength. In general, particles are more effectively fractionated into layers when the number of repeating cycles is higher. The last parameter is the timing of the pulse sequences of the PMF. Computational models were developed to determine DMF settings for different magnetic particle formulations. PEGylated, aminated, and starch coated SPIONs were used to represent SPIONs with different formulations and to confirm the prediction from the developed mathematical models.

Larger particles have a faster magnetic attraction rate and a slower diffusion rate than smaller particles. The time difference $|\Delta t_r|$ between varied sized SPIONs to be fully immobilized, indicates how particles are sized into layers. The performance of the DMF is expected to improve when $|\Delta t_r|$ increases. The $|\Delta t_r|$ between two particles of different sizes is affected by the pulse sequence of the applied PMF. The pulse sequence can be simplified into two parts, which are magnetic attraction and diffusion. The mass transport of SPIONs can be described by the Equation of Continuity.

$$\frac{dc}{dt} + \nabla \cdot \vec{J} = 0 \qquad \#(1)$$

The particle concentration c is dependent on time t and position x. The total flux $\vec{J}$ contains a diffusion $\vec{J}_D$ driven part and a force driven part $\vec{J}_F$, where $\vec{J} = \vec{J}_D + \vec{J}_F$. $\vec{J}_F \neq 0$ during magnetic attraction, and $\vec{J}_F = 0$ during diffusion. Magnetic attraction happens during a magnetic pulse and diffusion happens between pulses. The Equation of Continuity can be rewritten as the following equation (2) with diffusivity constant D independent of concentration.

$$\frac{dc}{dt} = D\nabla^2 c - \nabla \cdot (\vec{v}c) \qquad \#(2)$$

Except for the concentration c, all of the terms are independent of time. Therefore, the time dependent general solution for concentration c can be assumed as following, which was later confirmed by experiment.

$$c = c_0 e^{-\beta t_m} \qquad \#(3)$$

The constant β is proportionate to the magnetic attraction rate and is a function of particle size $R_p$ and position x. The time variable $t_m$ is the time for magnetic attraction, which is also known as the pulse width of the PMF. To solve for β, it is assumed a position dependent solution $r_{(x)}$, which its steady state solution is previously solved. The constant β can be expressed in the form of the following.

$$\beta = -Dr_{(x)}'' + \vec{v}\, r_{(x)}' + \vec{v}'\, r_{(x)} \qquad \#(4)$$

To solve for the particle size dependency of β, the total force acting on a single SPION can be described as the sum of magnetic attraction force $F_M$ and Stokes' drag force $F_D$. All other forces are assumed to be negligible compare to these two. The force balance is shown as follows:

$$F = F_M - F_D = \nabla(\vec{m}\cdot\vec{B}) - 6\pi\eta R_p \vec{v} \qquad \#(5)$$

where $\vec{B}$ is the applied magnetic field, η is the dynamic viscosity, $R_p$ is the radius of the SPION, and $\vec{v}$ is the particle drift velocity. Assuming uniformly magnetized spherical SPIONs, the magnetic moment $$\vec{m} = \frac{4}{3}\pi R_p^3 \vec{M}.$$

Accordingly, the force balance can be rewritten as follows:

$$F = \frac{4}{3}\pi R_p^3 \nabla(\vec{M}\cdot\vec{B}) - 6\pi\eta R_p \vec{v} \qquad \#(6)$$

The drift velocity $\vec{v}$ is assumed to only depend on position because the time to reach terminal velocity is very short, which is a result from the high surface to mass ratio of nanoparticles. Therefore, the nanoparticle velocity during a magnetic pulse can be calculated as follows:

$$\vec{v} = \frac{2R_p^2}{9\eta}\nabla(\vec{M}\cdot\vec{B}) \qquad \#(7)$$

The particle drift velocity $\vec{v}$ can be substituted into Equation of Continuity (2) and can be rewritten as the following equation (8)

$$\frac{dc}{dt} = \frac{kT}{6\pi\eta R_p}\nabla^2 c - \nabla\cdot\left(\left(\frac{2R_p^2}{9\eta}\nabla(M\cdot B)\right)c\right) \qquad \#(8)$$

Therefore, the particle size dependency of β in equation (4) can be shown as following.

$$\beta = \frac{g_{(x)}}{R_p} + h_{(x)}\frac{R_c^3}{R_p} \qquad \#(9)$$

$$\begin{cases} g_{(x)} = -\frac{kT}{6\pi\eta}\nabla^2 c \\ h_{(x)} = \frac{2}{9\eta}(\nabla(M\cdot B)\cdot\nabla c + c\nabla^2(M\cdot B)) \end{cases} \qquad \#(10)$$

The function $g_{(x)}$ is based on diffusion, and $h_{(x)}$ is the result of magnetic attraction. The equation was used to model the change in SPION concentration of differently sized particles during magnetic attraction.

Between the pulses of an applied PMF, SPIONs freely diffuse away from the magnetic source. Based on the Stoke-Einstein relationship, larger SPIONs have a slower diffusion rate than smaller SPIONs. The mass transport of the diffusion can be described as $$\frac{\partial C}{\partial t} = D\frac{\partial^2 C}{\partial x^2} \qquad \#(11)$$

The time dependent general solution for a fixed position can be described as $$c = c_0\left(1 - e^{-\frac{\alpha t_d}{R_p}}\right) \qquad \#(12)$$

where α is a positive constant, which is in proportionality to diffusivity coefficient D, and $t_d$ is the time between pulses.

Equations (3) and (12) are used to model the change in concentration of differently sized SPIONs with a given pulse sequence. The given pulse sequence is described by $t_m$, $t_d$, the strength of the magnetic pulse, and n which is the number of repeating cycles.

The times to fully capture differently sized SPIONs, $T_c(x, R_p)$, were estimated by calculating the times to reach 95% capture. For a fixed position, the remaining time, $T_r$, to reach 95% capture can be calculated for differently sized particles based on their current concentration.

$$T_r(c, R_p) = T_c(R_p) - T(c, R_p) \qquad \#(13)$$

The |ΔT$_r$| between differently sized SPIONs equals to the additional time required for the smaller SPIONs to reach 95% capture, which is used to determine the performance of the DMF. A larger |ΔT$_r$| indicates a larger time difference between the larger and the smaller particles to reach 95% capture, which improves how SPIONs are fractionated into layers.

Magnetic Attraction and Free Diffusion Study.

Figure 10:
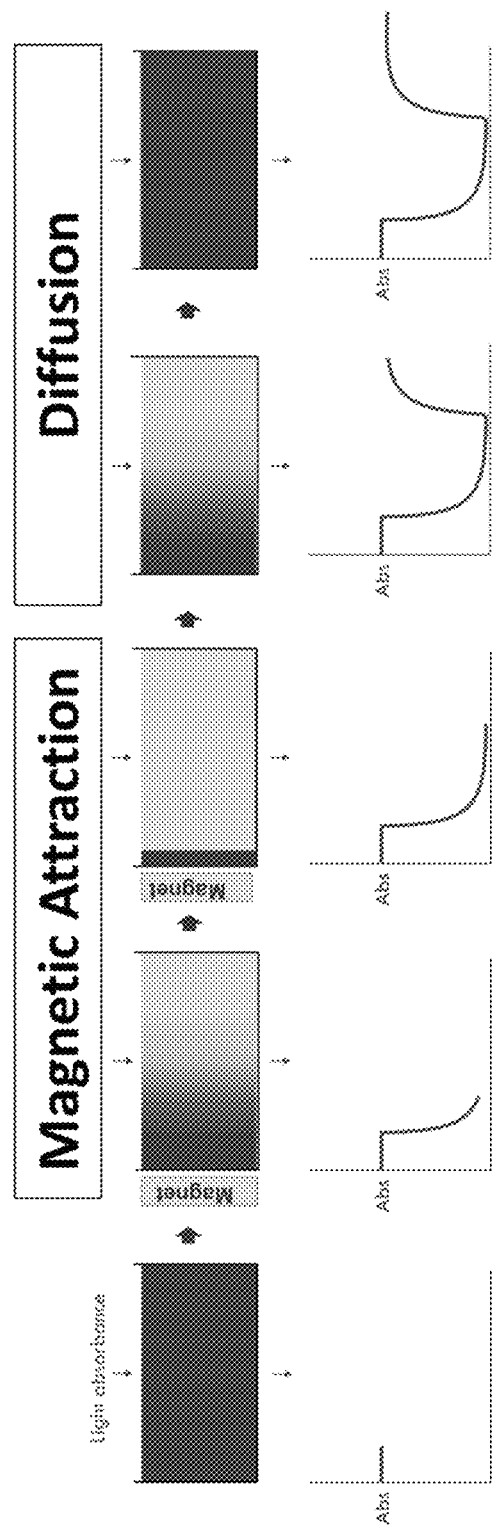
FIG. 10 shows a schematic view and charts of a magnetic attraction and diffusion study, where absorbance was measured across a static fluid suspension of SPIONs that was exposed to a magnetic field.

A bar magnet with a 0.25 T magnetic field strength was placed inside a 96-well plate with its magnetic pole pointing to an adjacent well. A SPION aqueous suspension was added into the well adjacent to the 0.25 T bar magnet. The change in SPION concentration was observed by measuring absorbance across a static fluid suspension. The concentration slowly reduced during magnetic attraction and slowly increased during diffusion. Absorbance at 450 nm was measured (SpectraMax i3; Molecular Device, US) at the center of the well with the SPION suspension. Measurements were taken every 10 minutes for 6 hours, as shown in FIG. 10.

After the magnetic attraction study, the 0.25 T bar magnet was removed from the 96-well plate. Absorbance measurements were taken at the center of the well every 10 seconds for minutes or at multiple positions inside the well every minute for 20 minutes, as shown in FIG. 10.

Figure 11:
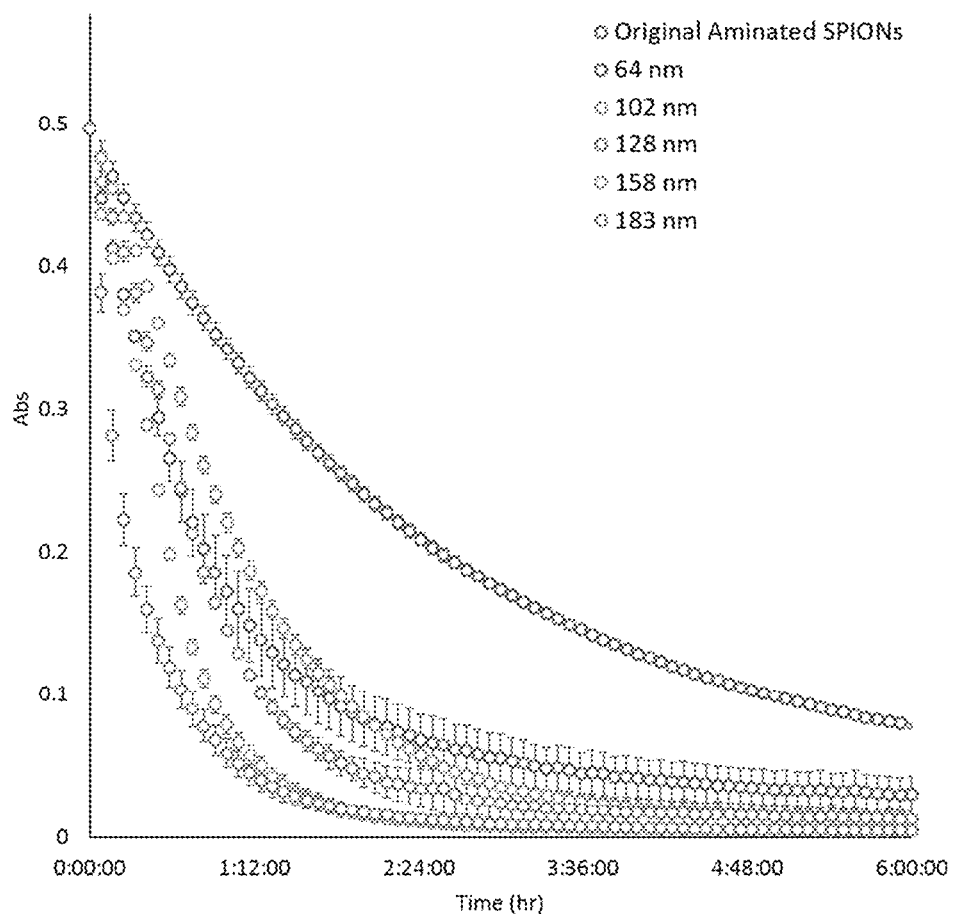
FIG. 11 shows a chart of absorbance measurements over time for aminated SPIONs of varying size with a constant magnetic field being applied.

As shown in FIG. 11, changes in concentration were measured over time when differently sized aminated SPIONs were captured by the bar magnet. Unfractionated aminated SPIONs had an average size of 137 nm and a PI of 0.18. The unfractionated particles were split into multiple fractions with DMF, resulting in fractionated particles having average sizes of 64, 102, 128, 158, and 183 nm. The PIs were 0.09, 0.06, 0.08, 0.08, 0.08, and 0.1, respectively.

Differently sized SPIONs demonstrated different magnetic attraction rates. These rates can be fitted with a single exponential (SE) model (except for the original, the largest, and the smallest SPIONs). The unfractionated SPIONs showed a distinguishable difference between the SE fit and multiple exponential (ME) fit. These particles also showed a significantly larger uncertainty range compared to the fractionated SPIONs. Similarly, the largest and the smallest fractionations are expected to have broader particle size distributions since particles above or below a certain size will all be collected by these two fractionations. The smallest SPIONs, however, can still be fitted by a model with a SE term with a constant term, which indicates 20% of a certain particle size was too small to be captured by the magnetic field.

Figure 12:
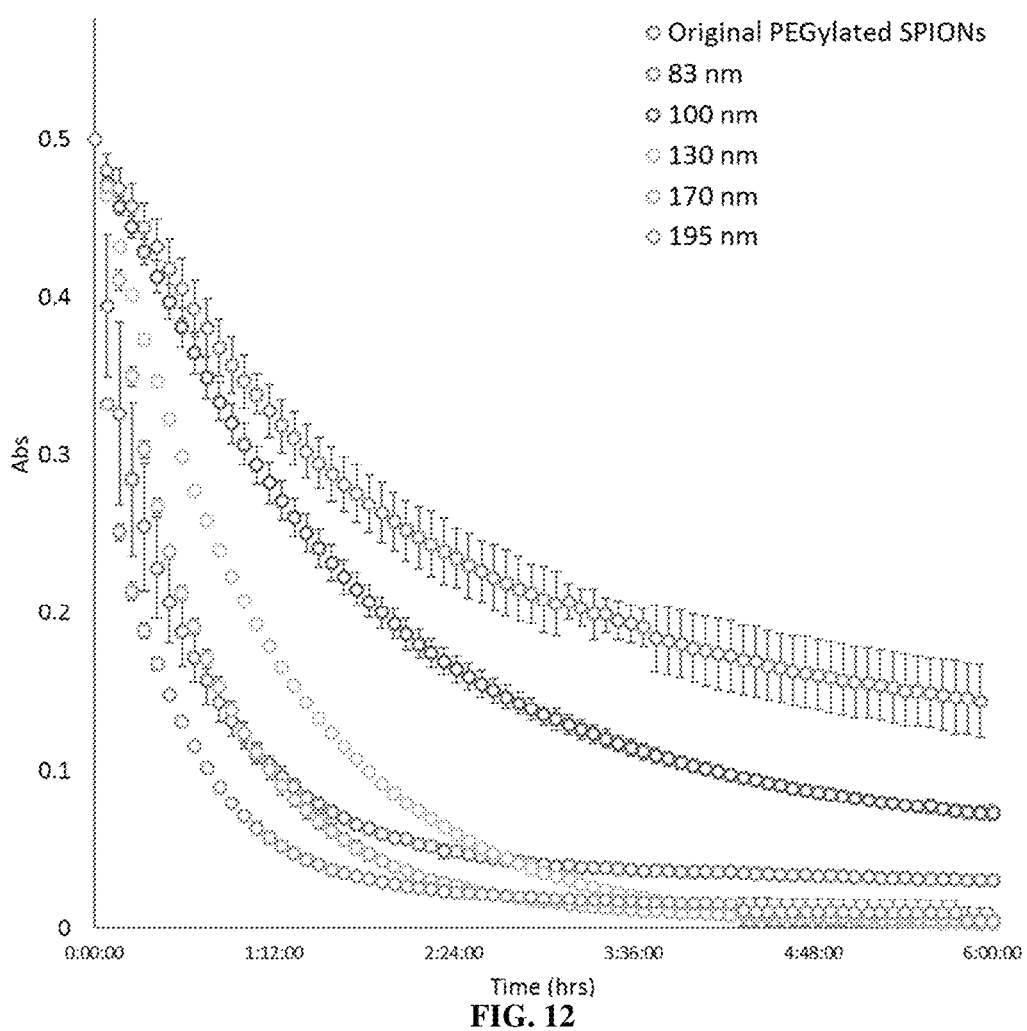
FIG. 12 shows a chart of absorbance measurements over time for PEGYlated SPIONs of varying size with a constant magnetic field being applied.
Figure 13:
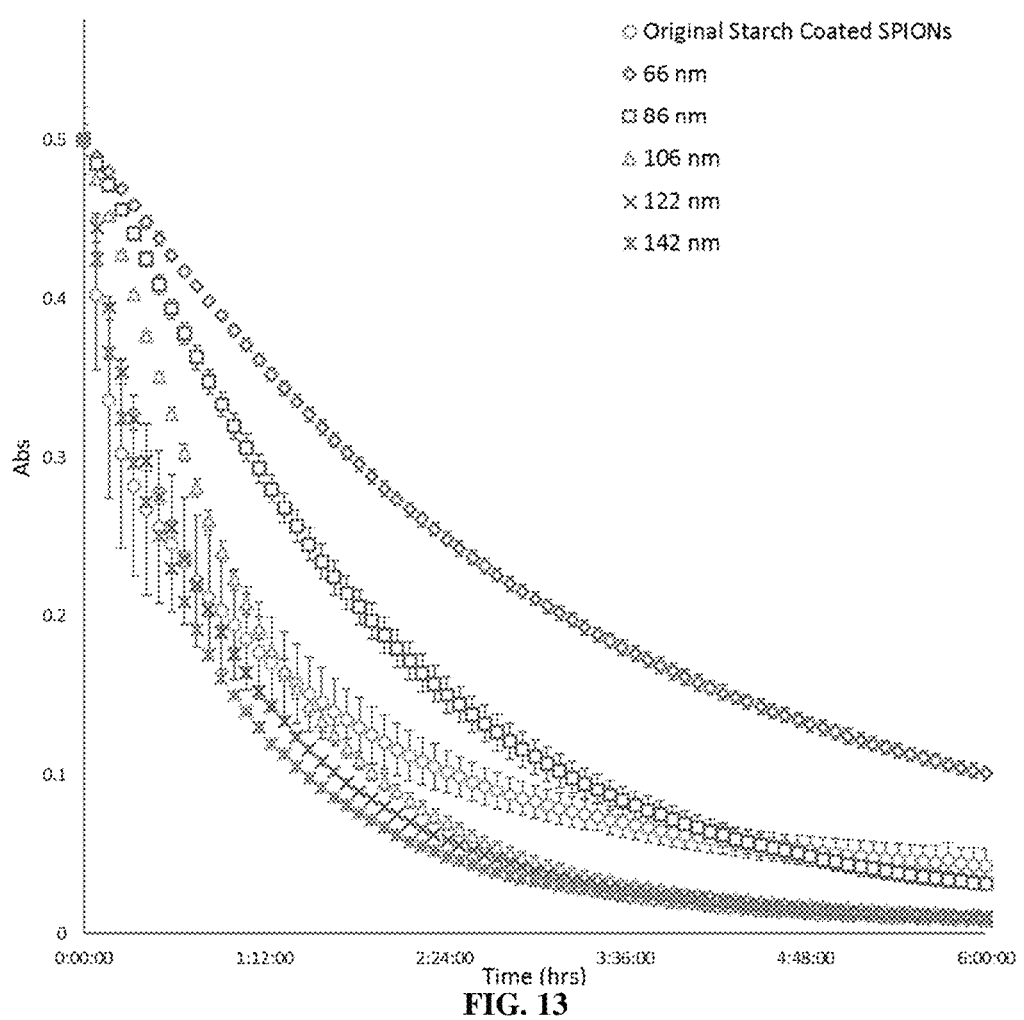
FIG. 13 shows a chart of absorbance measurements over time for starch-coated SPIONs of varying size with a constant magnetic field being applied.

Similar analyses were performed for particles with different surface treatments. As shown in FIG. 12, changes in concentration were measured over time when different sized PEGYlated SPIONs were captured by the bar magnet. As shown in FIG. 13, changes in concentration were measured over time when different sized starch coated SPIONs were captured by the bar magnet.

Therefore, equation (3) can be used model the magnetic attraction profile for differently sized monodisperse SPIONs with various formulations, and the β value can be extracted accordingly. The size dependency of β, equation (9), can be simplified for a fixed position and showed as following, where A and B are fitting parameters.

$$\beta = \frac{A}{R_p} - BR_p^2 \qquad \#(14)$$

The experimental results showed strong agreement with the mathematical model.

Figures 14A, 14B, 14C:
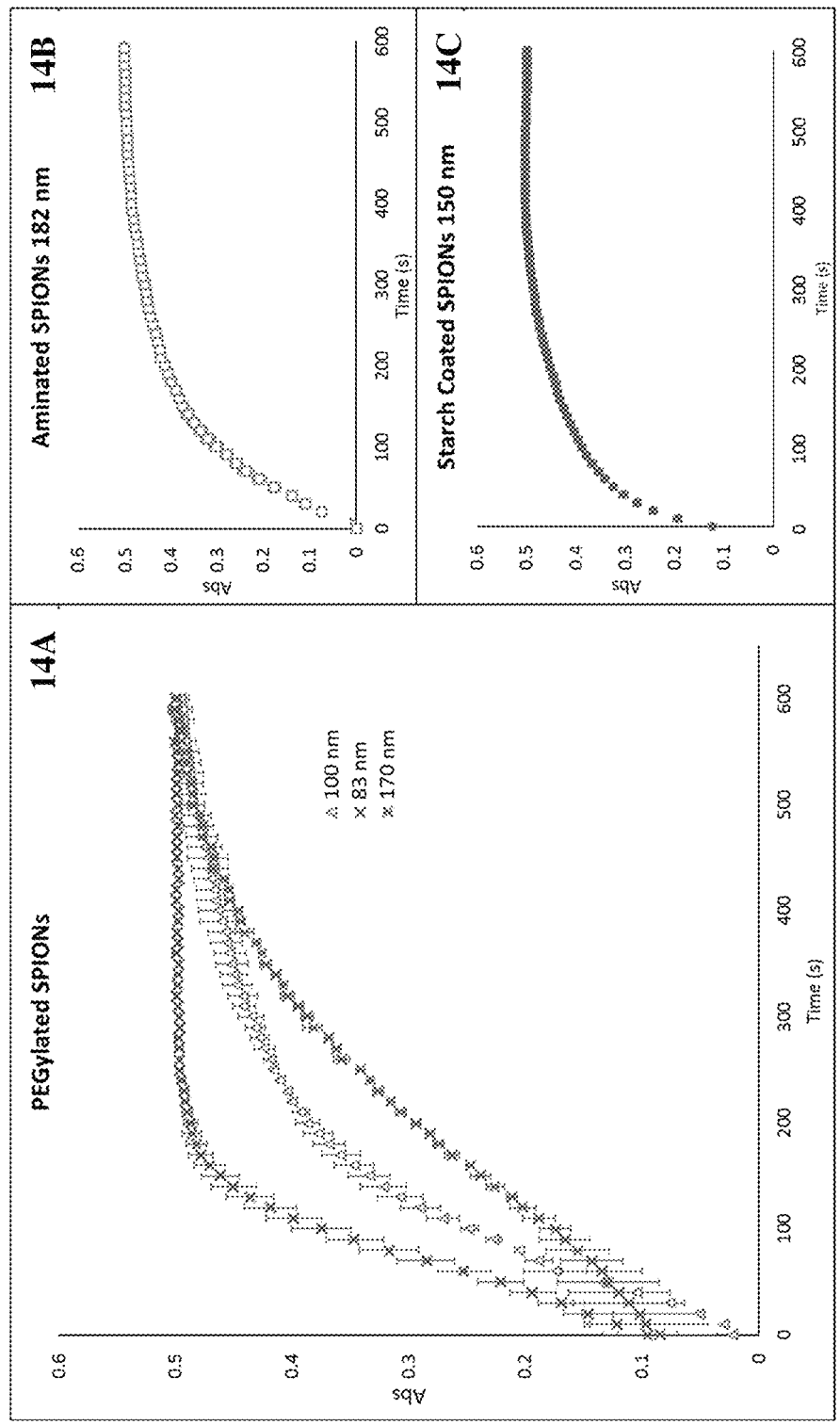
FIG. 14A shows a chart of absorbance measurements over time for PEGYlated SPIONs of varying size after being released from a constant magnetic field.
FIG. 14B shows a chart of absorbance measurements over time for aminated SPIONs of varying size after being released from a constant magnetic field.
FIG. 14C shows a chart of absorbance measurements over time for starch-coated SPIONs of varying size after being released from a constant magnetic field.

Diffusion of different size particles was accomplished by removing the bar magnet. As shown in FIGS. 14A, 14B, and 14C, different size particles showed different diffusion rates. The diffusion behavior can be modeled by equation (12) for different SPIONs formulations, but the measurement is most accurate when the rate is slow. Combined with the results for magnetic attraction, a complete concentration model during magnetic attraction and diffusion is described.

During magnetic attraction, concentration decreased due to the capture of SPIONs. On the other hand, SPION concentration increased during diffusion due to the absence of a magnetic field. The changes in SPION concentration in suspension with an applied PMF sequence can be calculated. Different pulse sequences can be applied based on these calculations. In particular, $|\Delta T_r|$ can be calculated for any given particle size and pulse sequence. For starch coated SPIONs between about 70 and about 140 nm, the $|\Delta T_r|$ was calculated, providing a setting having the highest value of $|\Delta T_r|$ with a pulse width of 70 seconds and 35 seconds between pulses. For aminated SPIONs between about 70 and about 140 nm, the $|\Delta T_r|$ was calculated, providing a setting having the highest value of $|\Delta T_r|$ with a pulse width of 80 seconds and 20 seconds between pulses. For PEGylated SPIONs between about 70 and about 140 nm, the $|\Delta T_r|$ was calculated, providing a setting having the highest value of $|\Delta T_r|$ with a pulse width of 110 seconds and 20 seconds between pulses.

As shown in FIG. 15, PdI was determined for various pulse sequences using uncoated SPIONs, including a pulse width of 90 seconds and 25 seconds between pulses, a pulse width of 30 seconds and 10 seconds between pulses, a pulse width of 120 seconds and 120 seconds between pulses, and a pulse width of 1000 seconds and 0 seconds between pulses.

The mathematical models showed strong agreement with the experimental results, which confirmed that the model can be used to predict the pulse sequence for different SPION formulations. The models were based on magnetic attraction and diffusion data, which can be acquired with the described experimental setup. $|\Delta T_r|$ values were calculated for different pulse sequences, which was used to indicate the performance of the DMF. As shown in FIGS. 16A, 16B, and 16C, DMF performance, as determined by PdI, improves when the value $|\Delta T_r|$ increases. Therefore, the models can be used to calculate pulse sequences based on magnetic attraction and diffusion data.

What is claimed is:

1. A method of separating magnetic nanoparticles, the method comprising the step of placing the magnetic nanoparticles in a periodic magnetic field, wherein the periodic magnetic field varies between a first magnetic field strength and a second magnetic field strength that is higher than the first magnetic field strength, and further comprising the step of applying a flowing fluid to the magnetic nanoparticles subsequent to the step of placing the magnetic nanoparticles in a periodic magnetic field, and further comprising the step of capturing fractionated layers of magnetic nanoparticles that are released during the applying step.

2. The method of claim 1, further comprising increasing the second magnetic field strength stepwise.

3. The method of claim 1, wherein the periodic magnetic field is generated by an alternating current and the second magnetic field strength is determined based on the amplitude of the alternating current.

4. The method of claim 1, wherein the periodic magnetic field is replaced by a continuous magnetic field when the flowing fluid is applied.

5. The method of claim 4, wherein the continuous magnetic field is decreased stepwise during the applying step to release fractionated layers of magnetic nanoparticles.

6. The method of claim 1, wherein a solvent of the flowing fluid is changed during the applying step to release fractionated layers of magnetic nanoparticles.

7. The method of claim 1, wherein the ionic strength of the flowing fluid is changed during the applying step to release fractionated layers of magnetic nanoparticles.

8. The method of claim 1, wherein the magnetic nanoparticles comprise two or more populations of magnetic nanoparticles having different compositions, and the magnetic nanoparticles form layers that are fractionated based on composition.

9. The method of claim 1, wherein the magnetic nanoparticles comprise superparamagnetic iron oxide.

10. A method of separating magnetic nanoparticles, the method comprising the step of placing the magnetic nanoparticles in a periodic magnetic field, wherein the periodic magnetic field varies between a first magnetic field strength and a second magnetic field strength that is higher than the first magnetic field strength, wherein the periodic magnetic field is present without flowing fluid, and further comprising the step of applying a flowing fluid to the magnetic nanoparticles after the step of placing the magnetic nanoparticles in a periodic magnetic field, and further comprising the step of capturing fractionated layers of magnetic nanoparticles that are released during the applying step.

11. The method of claim 10, further comprising increasing the second magnetic field strength stepwise.

12. The method of claim 10, wherein the periodic magnetic field is generated by an alternating current and the second magnetic field strength is determined based on the amplitude of the alternating current.

13. The method of claim 10, wherein the periodic magnetic field is replaced by a continuous magnetic field when the flowing fluid is applied.

14. The method of claim 10, further comprising the step of capturing fractionated layers of magnetic nanoparticles that are released during the applying step.

15. The method of claim 10, wherein a solvent of the flowing fluid is changed during the applying step to release fractionated layers of magnetic nanoparticles.

16. The method of claim 10, wherein the ionic strength of the flowing fluid is changed during the applying step to release fractionated layers of magnetic nanoparticles.

17. The method of claim 10, wherein the magnetic nanoparticles comprise two or more populations of magnetic nanoparticles having different compositions, and the magnetic nanoparticles form layers that are fractionated based on composition.

18. The method of claim 10, wherein the magnetic nanoparticles comprise superparamagnetic iron oxide.

19. A method of separating magnetic nanoparticles, the method comprising the step of placing the magnetic nanoparticles in a periodic magnetic field, wherein the periodic magnetic field varies between a first magnetic field strength and a second magnetic field strength that is higher than the first magnetic field strength, and further comprising the step of applying a flowing fluid to the magnetic nanoparticles subsequent to the step of placing the magnetic nanoparticles in a periodic magnetic field, wherein the periodic magnetic field is replaced by a continuous magnetic field when the flowing fluid is applied.

20. The method of claim 19, wherein the periodic magnetic field is present without flowing fluid.

* * * * *